US012656331B2

(12) United States Patent
Sivertsen et al.

(10) Patent No.: US 12,656,331 B2
(45) Date of Patent: Jun. 16, 2026

(54) STANDARDIZATION OF LATERAL FLOW ASSAY STRIP TEST RESULTS

(71) Applicant: Assaya LLC, Roswell, GA (US)

(72) Inventors: Clas Sivertsen, Lilburn, GA (US); Tom Sivertsen, Kristiansund (NO); Roy Larsen, Kristiansund (NO)

(73) Assignee: Assaya LLC, Lakeside, MT (US)

( * ) Notice: Subject to any disclaimer, the term of this patent is extended or adjusted under 35 U.S.C. 154(b) by 0 days.

(21) Appl. No.: 17/352,061

(22) Filed: Jun. 18, 2021

(65) Prior Publication Data

US 2025/0067724 A1     Feb. 27, 2025

(51) Int. Cl.
G01N 33/487          (2006.01)

(52) U.S. Cl.
CPC .............................. G01N 33/48771 (2013.01)

(58) Field of Classification Search
CPC ................................................ G01N 33/48771
See application file for complete search history.

(56) References Cited

U.S. PATENT DOCUMENTS

| | | |
|---|---|---|
| 5,075,078 A | 12/1991 | Osikowicz et al. |
| 5,308,775 A | 5/1994 | Donovan et al. |
| 5,717,778 A | 2/1998 | Chu et al. |
| 5,875,258 A | 2/1999 | Ortyn et al. |
| 5,968,839 A | 10/1999 | Blatt et al. |
| 6,061,128 A | 5/2000 | Zweig et al. |
| 6,267,722 B1 | 7/2001 | Anderson et al. |
| 6,394,952 B1 | 5/2002 | Anderson et al. |
| 6,664,071 B1 | 12/2003 | Windhab et al. |
| 7,177,235 B2 | 2/2007 | Rund |
| 7,236,428 B1 | 6/2007 | Morse |
| 7,267,799 B1 | 9/2007 | Borich et al. |
| 9,702,872 B1 | 7/2017 | Wang et al. |
| 9,857,372 B1 | 1/2018 | Pulitzer et al. |
| 9,857,373 B1 | 1/2018 | Pulitzer et al. |

(Continued)

FOREIGN PATENT DOCUMENTS

| | | |
|---|---|---|
| CN | 102482702 A | 5/2012 |
| CN | 102539735 A | 7/2012 |

(Continued)

OTHER PUBLICATIONS

Anfossi et al., Multiplex Lateral Flow Immunoassay: An Overview of Strategies towards High-throughput Point-of-Need Testing, Biosensors (Basel). Mar. 2019; 9(1): 2. (Year: 2018).

(Continued)

*Primary Examiner* — Jennifer Wecker
*Assistant Examiner* — Steven Ray Castaneda
(74) *Attorney, Agent, or Firm* — Nicholson De Vos Webster & Elliott LLP; Judith Szepesi

(57)                    ABSTRACT

A system including a processor and memory coupled to the processor. The memory is coupled to the processor for storing a local testing database having a test configuration profile with the test configuration profile having an equivalence curve that associates an intensity value with a standardized test result. A lateral flow assay strip reader is coupled to the processor for transmitting an LFA strip image to the processor. The processor determines a standardized test result based on an intensity value of a portion of the LFA strip image using an equivalence curve and provides the standardized test result.

19 Claims, 22 Drawing Sheets

(56) References Cited

U.S. PATENT DOCUMENTS

| | | |
|---|---|---|
| 10,197,558 B1 | 2/2019 | Saaski et al. |
| 10,823,746 B1 | 11/2020 | Busa et al. |
| 11,740,203 B2 | 8/2023 | Galen et al. |
| 11,802,868 B2 | 10/2023 | Pulitzer et al. |
| 12,094,603 B2 | 9/2024 | Sivertsen |
| 12,311,065 B1 | 5/2025 | Miller |
| 2001/0053336 A1 | 12/2001 | Hammer et al. |
| 2003/0021726 A1 | 1/2003 | Wu et al. |
| 2003/0040128 A1 | 2/2003 | Meador et al. |
| 2003/0120633 A1 | 6/2003 | Torre-Bueno |
| 2003/0139903 A1 | 7/2003 | Zweig et al. |
| 2003/0143530 A1 | 7/2003 | Klepp et al. |
| 2004/0122790 A1 | 6/2004 | Walker et al. |
| 2005/0008538 A1 | 1/2005 | Anderson et al. |
| 2005/0203353 A1 | 9/2005 | Ma et al. |
| 2005/0255001 A1 | 11/2005 | Padmanabhan et al. |
| 2005/0255600 A1 | 11/2005 | Padmanabhan et al. |
| 2006/0216832 A1 | 9/2006 | Nishikawa et al. |
| 2006/0223192 A1 | 10/2006 | Smith et al. |
| 2006/0246599 A1 | 11/2006 | Rosenstein et al. |
| 2006/0274145 A1 | 12/2006 | Reiner |
| 2006/0292040 A1 | 12/2006 | Wickstead et al. |
| 2007/0122914 A1 | 5/2007 | Curry |
| 2007/0143035 A1 | 6/2007 | Petruno |
| 2008/0186499 A1 | 8/2008 | Krauth |
| 2009/0061450 A1 | 3/2009 | Hunter |
| 2009/0074282 A1 | 3/2009 | Pinard et al. |
| 2009/0087926 A1 | 4/2009 | Hasegawa et al. |
| 2009/0155811 A1 | 6/2009 | Natan et al. |
| 2009/0312663 A1 | 12/2009 | John et al. |
| 2010/0045789 A1 | 2/2010 | Fleming et al. |
| 2010/0099115 A1 | 4/2010 | Mach et al. |
| 2010/0105024 A1* | 4/2010 | Xu .................. C12Q 1/6834 435/5 |
| 2010/0135857 A1 | 6/2010 | Hunter et al. |
| 2010/0267049 A1 | 10/2010 | Rutter et al. |
| 2010/0331651 A1 | 12/2010 | Groll |
| 2011/0213564 A1 | 9/2011 | Henke |
| 2011/0213579 A1 | 9/2011 | Henke |
| 2012/0071342 A1 | 3/2012 | Lochhead et al. |
| 2012/0115214 A1 | 5/2012 | Battrell et al. |
| 2012/0122236 A1 | 5/2012 | Tarpey |
| 2012/0123686 A1 | 5/2012 | Xiang et al. |
| 2012/0281970 A1 | 11/2012 | Garibaldi et al. |
| 2012/0282154 A1 | 11/2012 | Slowey et al. |
| 2013/0203043 A1 | 8/2013 | Ozcan et al. |
| 2013/0273645 A1 | 10/2013 | Waga |
| 2013/0288254 A1* | 10/2013 | Pollack ............. G01N 27/447 435/6.12 |
| 2013/0338243 A1 | 12/2013 | Kentsis et al. |
| 2014/0017812 A1 | 1/2014 | Smith et al. |
| 2014/0018779 A1 | 1/2014 | Worrell et al. |
| 2014/0154792 A1 | 6/2014 | Moynihan et al. |
| 2014/0227681 A1 | 8/2014 | Fleming et al. |
| 2014/0278832 A1 | 9/2014 | Glavina et al. |
| 2014/0324373 A1 | 10/2014 | Xiang et al. |
| 2014/0339100 A1* | 11/2014 | Malecha .......... G01N 33/48771 205/792 |
| 2015/0010992 A1 | 1/2015 | Fleming et al. |
| 2015/0099306 A1 | 4/2015 | Ku |
| 2015/0244852 A1 | 8/2015 | Erickson et al. |
| 2015/0338387 A1 | 11/2015 | Ehrenkranz |
| 2015/0350605 A1 | 12/2015 | Price et al. |
| 2016/0030613 A1 | 2/2016 | Paul et al. |
| 2016/0085913 A1 | 3/2016 | Evans et al. |
| 2016/0131645 A1 | 5/2016 | Wang |
| 2016/0157598 A1 | 6/2016 | Anelevitz |
| 2016/0178607 A1 | 6/2016 | Husheer et al. |
| 2016/0188937 A1 | 6/2016 | Tyrrell et al. |
| 2016/0265032 A1 | 9/2016 | Sethi et al. |
| 2016/0356800 A1 | 12/2016 | Glavina et al. |
| 2016/0356801 A1 | 12/2016 | Glavina et al. |
| 2016/0370366 A1 | 12/2016 | Fleming et al. |
| 2017/0049915 A1 | 2/2017 | Brais et al. |
| 2017/0160258 A1 | 6/2017 | Hengstler et al. |
| 2017/0184586 A1 | 6/2017 | Hopper |
| 2018/0031551 A1 | 2/2018 | Karlovac et al. |
| 2018/0071741 A1 | 3/2018 | Kelly et al. |
| 2018/0106789 A1 | 4/2018 | Pulitzer et al. |
| 2018/0107790 A1 | 4/2018 | Pulitzer et al. |
| 2018/0149600 A1 | 5/2018 | Farrell |
| 2018/0164222 A1 | 6/2018 | Pulitzer et al. |
| 2018/0246038 A1* | 8/2018 | Hunter ................. G01N 21/274 |
| 2018/0259449 A1 | 9/2018 | Poulsen et al. |
| 2018/0293350 A1 | 10/2018 | Dimov et al. |
| 2018/0348198 A1 | 12/2018 | Broadwell |
| 2018/0372734 A1 | 12/2018 | Pfenninger et al. |
| 2019/0070324 A1 | 3/2019 | Hardin et al. |
| 2019/0096516 A1 | 3/2019 | Pulitzer et al. |
| 2019/0122768 A1 | 4/2019 | Pulitzer et al. |
| 2019/0224685 A1 | 7/2019 | Benenati |
| 2019/0229907 A1* | 7/2019 | Nicolson ............... H04L 63/166 |
| 2019/0267822 A1 | 8/2019 | Voit et al. |
| 2019/0317115 A1 | 10/2019 | Maclean et al. |
| 2019/0339264 A1* | 11/2019 | Gary ................ G01N 33/54386 |
| 2019/0369094 A1 | 12/2019 | Ishikawa et al. |
| 2020/0330979 A1 | 10/2020 | Cyr et al. |
| 2020/0386753 A1 | 12/2020 | Somes et al. |
| 2020/0408715 A1* | 12/2020 | Galen ............. G01N 27/44721 |
| 2021/0086177 A1 | 3/2021 | Lin |
| 2021/0132035 A1 | 5/2021 | Adelman |
| 2021/0172945 A1* | 6/2021 | Armbruster ........ G01N 21/8483 |
| 2021/0263018 A1 | 8/2021 | Taran |
| 2021/0293688 A1 | 9/2021 | Chang et al. |
| 2021/0319911 A1 | 10/2021 | Hall et al. |
| 2021/0327056 A1 | 10/2021 | Needham et al. |
| 2021/0389233 A1 | 12/2021 | Hatamian |
| 2022/0055036 A1 | 2/2022 | Tycon |
| 2022/0091114 A1 | 3/2022 | Levin et al. |
| 2022/0178920 A1 | 6/2022 | Howard |
| 2022/0254027 A1 | 8/2022 | Lin et al. |
| 2022/0254133 A1 | 8/2022 | Adsul et al. |
| 2022/0258155 A1 | 8/2022 | Ren et al. |
| 2022/0296755 A1 | 9/2022 | Wurmfeld et al. |
| 2022/0304560 A1 | 9/2022 | Jackson et al. |
| 2022/0399109 A1 | 12/2022 | Sivertsen |
| 2022/0404354 A1 | 12/2022 | Robinson et al. |
| 2022/0405551 A1 | 12/2022 | Jain et al. |
| 2022/0412961 A1 | 12/2022 | Jolly et al. |
| 2023/0213452 A1 | 7/2023 | Minobe et al. |
| 2023/0274538 A1 | 8/2023 | Sia et al. |
| 2023/0351754 A1 | 11/2023 | Satish et al. |
| 2024/0363206 A1 | 10/2024 | Mayer |
| 2024/0387010 A1 | 11/2024 | Sivertsen et al. |
| 2024/0402198 A1 | 12/2024 | Sivertsen |
| 2024/0404658 A1 | 12/2024 | Sivertsen et al. |
| 2024/0412829 A1 | 12/2024 | Sivertsen et al. |
| 2024/0424160 A1 | 12/2024 | Sivertsen et al. |
| 2024/0428905 A1 | 12/2024 | Sivertsen |

FOREIGN PATENT DOCUMENTS

| | | |
|---|---|---|
| CN | 106680496 A | 5/2017 |
| CN | 211280092 U | 7/2020 |
| EP | 0480208 A2 | 4/1992 |
| EP | 2839264 A1 | 2/2015 |
| TW | 201833554 A | 9/2018 |
| TW | M588797 U | 1/2020 |
| WO | 2013/119266 A1 | 8/2013 |
| WO | 2013/158504 A1 | 10/2013 |
| WO | 2020/174895 A1 | 9/2020 |
| WO | 2020/251460 A1 | 12/2020 |

OTHER PUBLICATIONS

AssayGenie, Rapid covid19 antibody detection test principles and methods, published: 2020, https://www.assaygenie.com/rapid-covid 19-antibody-detection-tests-principles-and-methods (Year: 2020).

Azzi et al, Rapid Salivary Test suitable for a mass screening program to detect SARS-CoV-2: A diagnostic accuracy study, Journal of Infection, vol. 81, Issue 3, Sep. 2020, pp. e75-e78 (Year: 2020).

(56) References Cited

OTHER PUBLICATIONS

Badi et al., The Effect of Gold Salt Concentration in the Production of Gold Nanospheres, Jan. 2020, Journal of Applied Mathematics and Physics (Year: 2020).

Baker et al., The SARS-COV-2 Spike Protein Binds Sialic Acids and Enables Rapid Detection in a Lateral Flow Point of Care Diagnostic Device, 2020, vol. 6, 2046-2052 (Year: 2020).

Contreras-Aguilar, Changes in Saliva Analytes in Dairy Cows during Peripartum: A Pilot Study, Mar. 9, 2021, Animals, vol. 11, issues 3 (Year: 2021).

Independent Forensics, Developmental Validation of RSID-Urine, Mar. 2021, Independent Forensics, https://www.ifi-test.com/rsid-urine/ (Year: 2021).

Larsen et al., Fluorometric determination of uric acid in bovine milk, 2010, Journal of Dairy Research, vol. 77, 438-444 (Year: 2010).

Old et al., Developmental Validation of RSIDTM-Saliva: A Lateral Flow Immunochromatographic Strip Test for the Forensic Detection of Saliva, J Forensic Sci, Jul. 2009, vol. 54, No. 4 (Year: 2009).

Richardson et al., Amylase in Cow's Milk, 1936, Journal of Dairy Science, vol. 19, Issue 12, 761-772 (Year: 1936).

StatTechnologies, Adulteration Test Strips, 2017, StatTechnologies, https://stat-technologies.com/product/adulteration-test-strips/ (Year: 2017).

Stuart Patton, Some Practical Implications of the Milk Mucins, 1999, Journal of Dairy Science, vol. 82, Issue 6, 1115-1117 (Year:1999).

Thao et al. (American Clinical Society, 2017, p. 6781-6786).

Zhou et al. Paper electrode integrated lateral flow immunosensor for quantitative analysis of oxidative stress induced DNA damage, 2014, Analyst, 139(11), 2850-2857 (Year: 2014).

Urusov AE et al. (2019) Towards Lateral Flow Quantitative Assays: Detection Approaches. Biosensors, 9(3), 16 pgs; https://doi.org/10.3390/bios9030089 (Year: 2019).

Correa, M. E. et al, Pregnancy Hypertension: An International Journal of Women's Cardiovascular Health 2017, 750-53. (Year: 2017).

De Silva, D. A. et al, Journal of Obstetrics and Gynaecology Canada 2014, 36, 605-612. (Year: 2014).

Filippini, D. et al, Analyst 2006, 131, 111-117. (Year: 2006).

Grant et al. (May 7, 2020, Intellectual Ventures Lab, p. 1-11).

Hou, Y. et al, Nanoscale Research Letters 2017, 12, paper 291, 13 pages. (Year: 2017).

Lin, C.-S. et al, Optik 2004, 115, 363-369. (Year: 2004).

Magiati, M. et al, Microchimica Acta 2018, 185, paper 314, 9 pages. (Year: 2018).

O'Farrell, B., in Lateral Flow Immunoassay 2009, Wong, R. C. et al. (eds.), Humana Press, New York, 1-33. (Year: 2009).

Panic, G. et al, Parasites & Vectors 2019, 12, paper 298, 7 pages. (Year: 2019).

Tucker, K. et al., Pregnancy Hypertension 2018, 12, 161-168. (Year: 2018).

Waters, L. C. et al., Journal of Hazardous Materials 1995, 43, 1-12. (Year: 1995).

Waugh, J. J. S. et al., BJOG: an International Journal of Obstetrics and Gynaecology 2005, 112, 412-417. (Year: 2005).

Xu, Y. et al, Analytical Chemistry 2018, 90, 708-715 with 13 pages of supporting information. (Year: 2018).

* cited by examiner

1330

1332

Receive X Images

1334

For Each Image Straighten the Image

1336

For Each of the X Images Find Median Test Line Intensity

1338

Return Median Test Line Intensity

1400

1500

1510 Receive Test Info

1520 Scan Test Cassette

1530 Create and Store Profile

1540 Repeat?

Yes

No

1550 Receive Operator Thresholds

1560 Upload to Database

STANDARDIZATION OF LATERAL FLOW ASSAY STRIP TEST RESULTS

BACKGROUND

The present invention generally relates to measurement standardization and more specifically, to a standardization of lateral flow assay ("LFA") strip test result system and method.

Coronavirus Disease 2019 ("COVID-19") is spreading throughout the country and the world caused by the spread of a novel coronavirus called SARS-COV-2 often also referred to as SARS2. With the rapid spread of the disease, testing quickly, accurately, and efficiently is becoming more important. Testing may be performed using an LFA strip present in an assay tube or cassette. The results of the test are determined by examining the LFA strip by looking for the presence of, for example, visual stripes on the LFA strip. Traditionally, LFA strip test results have been presented in binary fashion, either as a positive result or a negative result. Results indicative of a magnitude of viral load have not been available by using an LFA strip.

SUMMARY

Embodiments of the present invention are directed to a system including a processor and memory coupled to the processor. The memory is coupled to the processor for storing a local testing database having a test configuration profile with the test configuration profile having an equivalence curve that associates an intensity value with a standardized test result. A lateral flow assay ("LFA") strip reader is coupled to the processor for transmitting an LFA strip image to the processor. The processor determines a standardized test result based on an intensity value of a portion of the LFA strip image using an equivalence curve and provides the standardized test result.

Further embodiments are directed to a method that reads a lateral flow assay ("LFA") strip, using an imaging device, to generate an LFA strip image. The method determines, using a processor, a standardized test result based on an intensity value of a portion of the LFA strip image that comprises a test line comprising a plurality of columns using an equivalence curve. The method provides, using the processor, the standardized test result.

Further embodiments of the present invention are directed to a method. The method builds an equivalence curve for a lateral flow assay ("LFA") strip. The method receives, by a processor, test information for the LFA strip and receives, by the processor, an image of the LFA strip. The method receives, by the processor, a known concentration of a viral load placed onto the LFA strip and associates, by the processor, an intensity of a portion of the image of the cassette with the known concentration of the viral load placed onto the LFA strip and a standardized value. The method repeats one or more of the previous steps, by the processor, until the equivalence curve is created and stores, by the processor, the equivalence curve.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
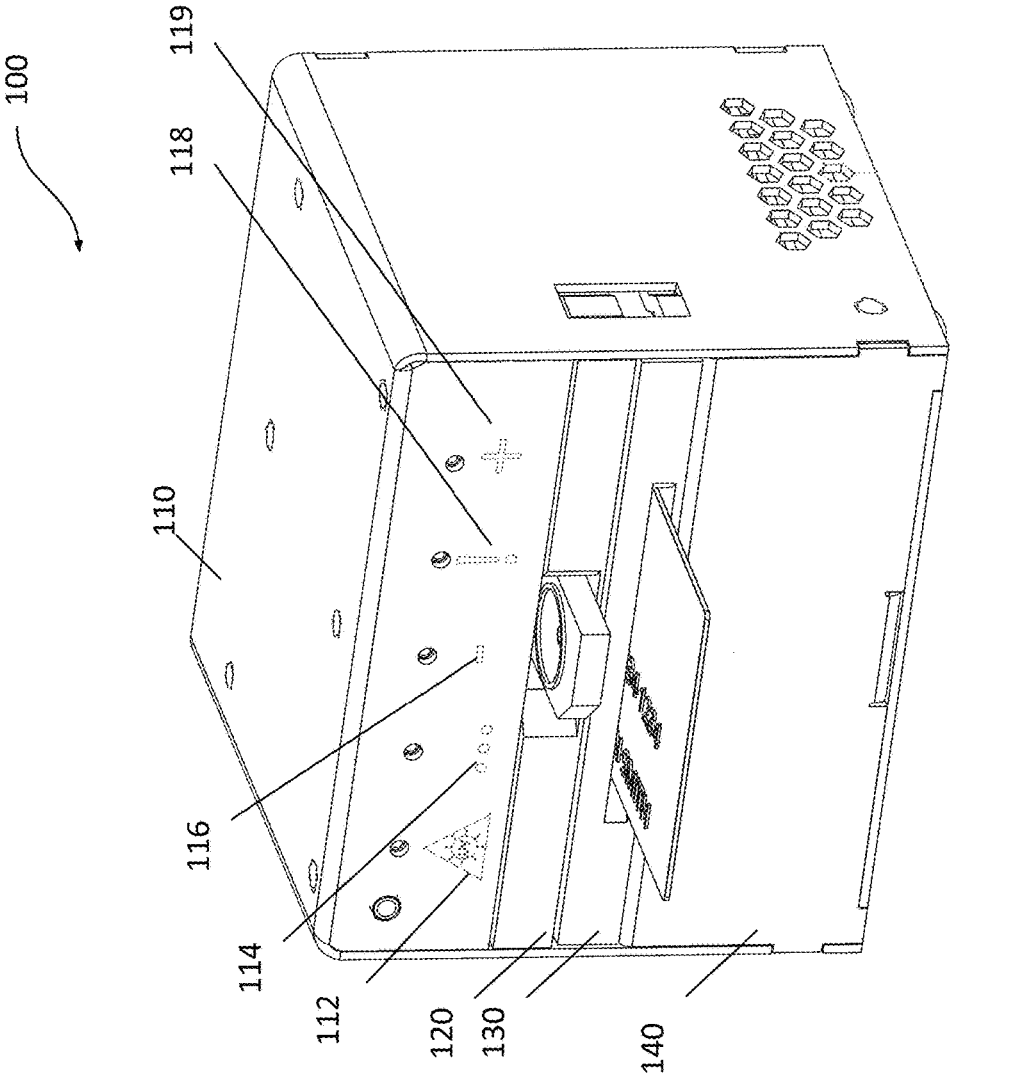
FIG. 1 depicts an orthogonal view of a testing device according to an embodiment of the present invention.

The diagrams depicted herein are illustrative. There can be many variations to the diagrams or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two-or three-digit reference numbers. With minor exceptions, the leftmost digit(s) of each reference number corresponds to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Turning now to an overview of technologies that are more specifically relevant to aspects of the invention, as previously stated, SARS-COV-2 is spreading rapidly around the country and around the world resulting in a large portion of the population being at risk of developing COVID-19. It is imperative to test, often repeatedly, the population for SARS-COV-2, and present testing systems are inadequate.

Present testing systems often require a nasal swab to get samples from a patient. This is very uncomfortable for the patient and requires a doctor, nurse, or technician to get very close to the patient, putting her at risk for developing COVID-19. Some tests exist that involve blood or saliva, but those tests, like the nasal tests, often take a great deal of time in order to get results back to the patient. By the time that test results are returned to the patient, the patient, if positive for SARS-COV-2, may have infected dozens of others, thus spreading the illness.

A polymerase chain reaction ("PCR") test is currently the gold standard, as it is currently the most sensitive type of test. A cycle threshold ("Ct") value is typically used as the measure for test results in PCR tests. For SARS-COV-2 tests this value is increasingly published on test reports and is useful as a marker for the severity of the disease in patients with COVID-19 illness, as it is generally proportional to the viral load found in a sample from a patient. Ct refers to the number of cycles needed to amplify viral RNA to reach a detectable level. Several studies point to a telling link between this viral load marker and severity of disease. One study found an association between lower Ct values and progression to severe disease and complications. The investigators found significant correlations between Ct values and severe disease or death. Ct value can also be used to track the progression of an infection in a particular patient, especially if it is recorded and plotted across a number of tests for a particular patient.

One retrospective cohort study evaluated a large number of patients admitted to the hospital with a positive SARS-COV-2 test and viral pneumonia. Investigators used PCR testing to group patients into three genomic load cohorts: low (Ct≥35), intermediate (25<Ct<35), and high (Ct≤25). Following the patients for an average of 25 days, they determined that high genomic load at presentation predicted adverse outcomes independent of age, comorbidities, and severity of illness at presentation. Thus Ct is an important value that provides useful guidance as to the severity of COVID-19 illness.

Unfortunately, present LFA strip testing does not provide a Ct value, providing a simple positive or negative result depending upon the presence or absence of a test line on the LFA strip. Also, there is presently not any industry standard that describes the intensity of LFA strip testing across multiple vendors. Lastly, the intensity of a testing line from the same patient when tested across multiple vendor's LFA strips may vary significantly.

Turning now to an overview of the aspects of the invention, embodiments of the present invention are able to analyze characteristics of the test line (shown, for example, later in FIG. 6 as test line 650) in order to determine an equivalent cycle time ("Ct") value ("eCt"). Using curves determined through laboratory analysis, a testing device known as an intelligent analyzer eXpress ("iaX"), described below and manufactured by Apollo BioTech co., ltd. and branded assaya™, measures the intensity of the test line, where intensity can be measured visually or based on conductivity of the test line, and based on the intensity calculates an eCt that approximates the Ct result that would be found had a PCR test been performed on the same patient. Furthermore, embodiments of the present invention, determine this intensity value regardless of any variation in characteristics of the paper that makes up the LFA strip. This eCt value can then be used by healthcare professionals to assist in determining severity of infection and inform treatment options.

While the discussion in this description uses testing for SARS-COV-2 to discuss embodiments of the invention, those skilled in the art after reading this specification will appreciate that similar techniques can be used to standardize testing of multiple viruses or substances to standardize test results. These test results are standardized across testing techniques and across testing products and protocols of a range of test manufacturers. Regardless of test kit maker, health care professionals can be provided with a standardized result that has meaning beyond positive and negative results.

As previously mentioned, embodiments of the present invention can be implemented with a testing device that provides fast results. RAPID™ (which is an acronym for Reliable Accurate Practical Inexpensive Diagnostics) antigen and antibody tests and associated reading methods become crucial in improving the speed and quality of test data. Because the invention described herein uses a computerized reader rather than relying on human interpretation, systems and method described herein are not only more accurate in differentiating a positive from a negative from an invalid test result, but they may also visually read and store the actual concentration of the pathogen so that analytics can be performed across a large number of patients, which can in turn be used by government, research institutes, vaccine developers, and pandemic planners implementing prevention measures to reduce the spread of future diseases. This concentration, which is based on intensity of the test line, is also used to determine an eCt that can be used by health professionals to guide treatment.

In addition, the testing device of the present invention includes a powerful computer that can store testing protocols for a full gauntlet of different tests as well as equivalence curves that are used to convert intensity of a read test line to an eCt or other appropriate standardized, equivalent results. Tests are not limited to COVID-19 testing, but can include reading any type of test strip, or test carriage, for any type of disease, syndrome, virus, or bacteria. The results of any of these tests are uploaded to a central database for providing to the patient and for later use and analysis. Data collected in the central database may be anonymized for data mining purposes.

The testing device may also communicate with a web browser or dedicated app on a patient's mobile phone, tablet, or computer for providing the patient with test results and logging.

FIG. 1 depicts an orthogonal view of a testing device 100 according to an embodiment of the present invention. The testing device 100 is enclosed by a case 110. The case 110 includes a plurality of electronics for analyzing a lateral flow assay ("LFA") strip present in an assay tube or cassette. References to LFA throughout this specification include references to lateral flow tests, rapid antigen tests, and antigen card tests. A removable sample carrier 120 has an opening in which the assay tube, cassette, or card is placed. During the remainder of this description, whenever the term "cassette" is used that term includes any of an assay tube, cassette, or card. The LFA strip provides indicators (stripes at various places along the LFA strip) that indicate the presence of analytes present in a sample. The testing device 100 includes an LFA strip reader having a plurality of LED's at a variety of wavelengths that shine upon the sample and a camera that images the sample, sending the image to a computer present in the testing device 100 for analysis. As a relatively powerful computer receives the image of the LFA strip, the computer can adjust for any misalignment of samples or changes to characteristics of the paper that the LFA strip is made from. In addition, in exemplary embodiments of the invention, one of the light sources can provide UVC light for sterilizing the testing device 100 prior to a new assay tube or cassette being placed in the testing device 100.

The camera in the device not only reads the LFA strip, but also any barcode, providing both images to the computer in the testing device 100. When a barcode is not present, the camera provides a visual feature to the computer. Such a visual feature may be the shape of the inserted cassette, text on the cassette, presence or absence of one or more barcodes, data matrices or QR codes, or one or more colors present on the cassette, for example. The computer may then associate the unique ID with the test results and upload the results to a central database where it is provided back to the patient and/or caregiver.

As the testing device 100 may be a headless device (one lacking a keyboard or screen for input and a screen or printer for output), a plurality of indicators on an indication panel is present on the front of the testing device 100 for indicating, for example, disinfecting in process 112, testing-in-process 114, negative results 116, invalid 118, or positive results 119 from the sample.

Testing device 100 also includes a patient identification reader for reading patient identification information, such as card reader 130 for reading an identification card from a patient to associate the patient with the received assay tube or cassette. In an exemplary embodiment of the invention, the card reader may be a smart card reader to read a government issued ID, such as a passport, national ID card, health card, or smart driver's license or it may read a credit card associated with the patient. Those skilled in the art will appreciate after reading this disclosure that other readers may also be used: for example, near field communication from a patient's device, such as her mobile phone, may be used to associate the patient with the sample or a magnetic strip may be read from a credit card lacking a smart chip. These variations are all contemplated to be used. In this way, when using the testing device 100 with cassettes that lack a unique identifier, the test result remains associated with the patient. No user input is needed beyond the identification card.

As stated previously, the testing device 100 may be in communication over, for example, Ethernet, WiFi, or mobile communications (such as 3G, 4G, and 5G, for example, to a central database. Test results, including standardized results, such as eCt, are linked to the patient at the testing device 100 and provided to the central database following a test. The test results may then be further shared with the patient's healthcare provider and/or directly to the patient. A rich database of information is developed in the central patient database, and following anonymization, may be mined for demographic or other information relating to the test being taken.

Linking the testing device 100 to a central server also provides an additional benefit, as new tests are developed that use LFA strips, new profiles for tests may be downloaded, either automatically or pushed manually, from a central test database to the testing device 100. Thus, there is no need for expensive field technicians to update the testing device 100. Such updates happen automatically. These profiles include not only testing information, but also equivalence curves used by testing device 100 to convert intensity measurements of the test line to an equivalent, standardized result.

Figure 2:
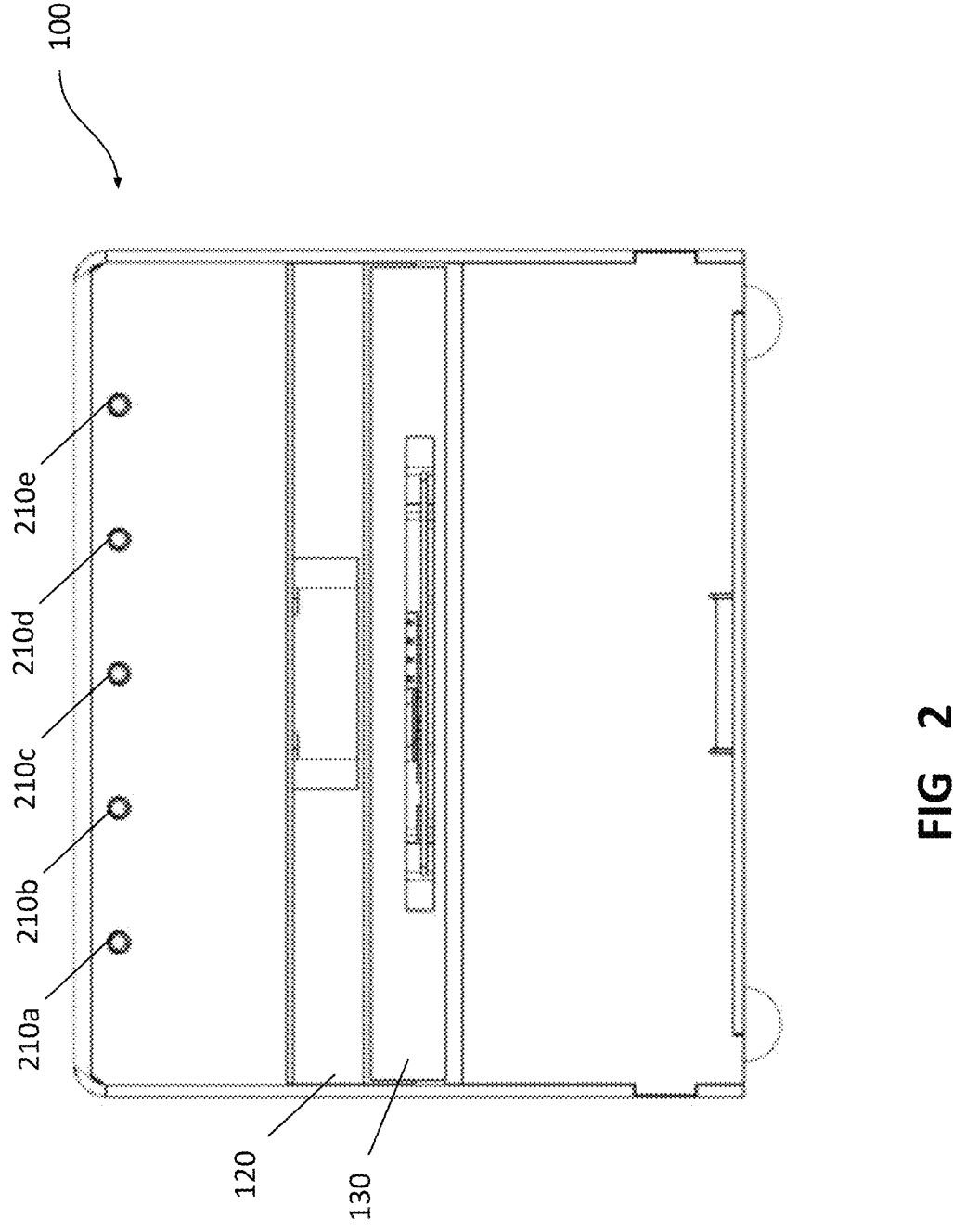
FIG. 2 depicts a front view of the testing device according to an embodiment of the present invention.

FIG. 2 depicts a front view of the testing device 100 according to an embodiment of the present invention. The front view again shows the removable sample carrier 120 for holding a cassette or assay tube and the card reader 130. In addition, five indicators, for example LED's, provide test results to a patient who is using the test device 100. In an exemplary embodiment, a sterilization indicator 210*a* that shows when sterilization activity is occurring within testing device 100, connectivity indicator 210*b*, positive result indicator 210*c*, fault indicator 210*d*, and negative result indicator 210*e* may be provided. An additional power indicator with a power switch 440 may be included to power the testing device 100 on and off.

Figure 3:
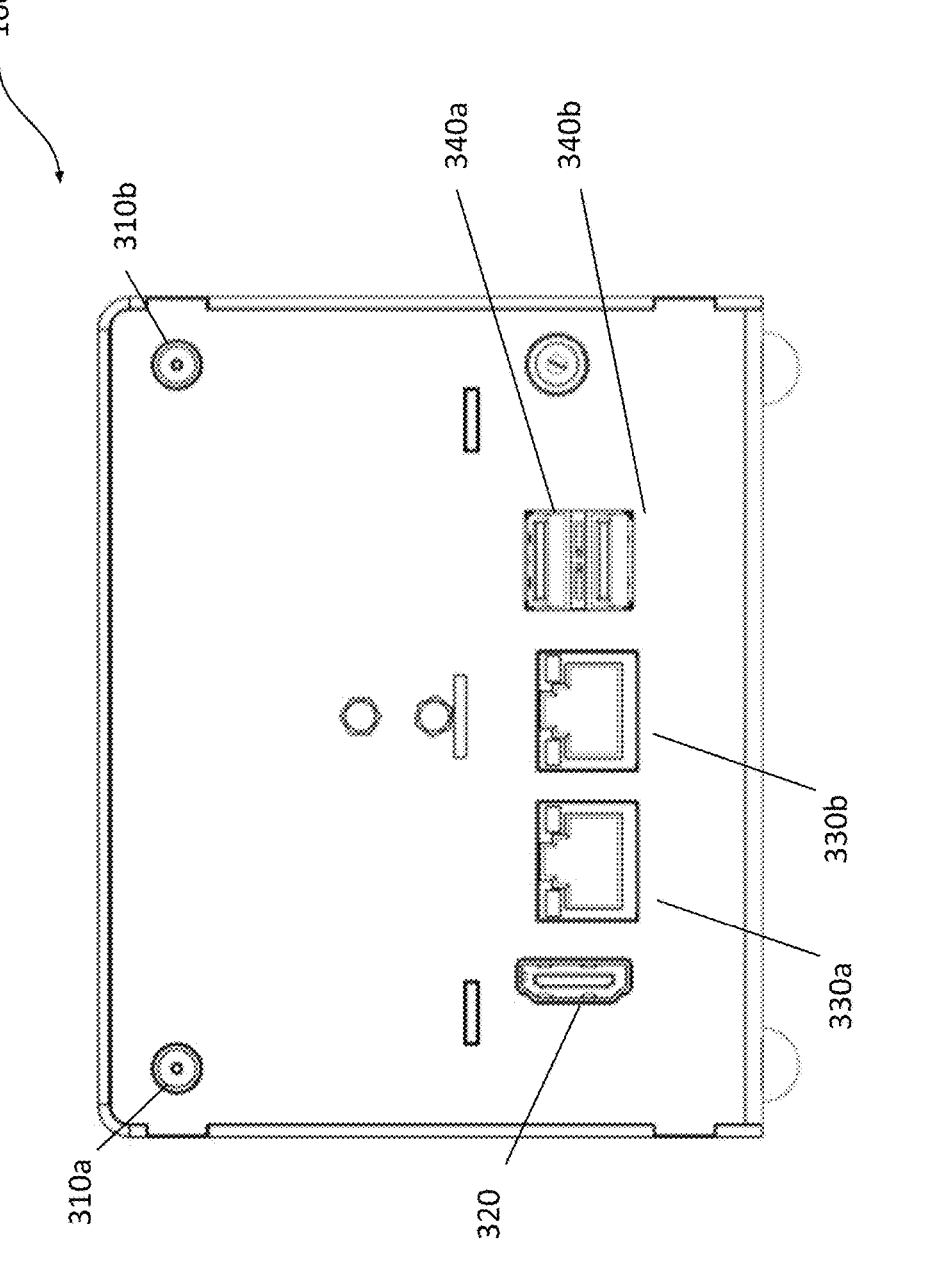
FIG. 3 depicts a back view of the testing device according to an embodiment of the present invention.

FIG. 3 depicts a back view of the testing device 100 according to an embodiment of the present invention. The back view of the testing device 100 shows various connectivity features present in an exemplary testing device 100. Testing device 100 may have a port for a display, such as HDMI port 320, Ethernet ports 330*a* and 330*b*, and USB ports 340*a* and 340*b*. Thus, while the testing device is primarily designed to be headless, if placed in a lab or a doctor's office the testing device also supports connection to a monitor and a keyboard. Results may then be shared with a healthcare professional on the display, and since the testing device 100 includes a full computer, it can support additional functions for the healthcare provider.

Figure 4A:
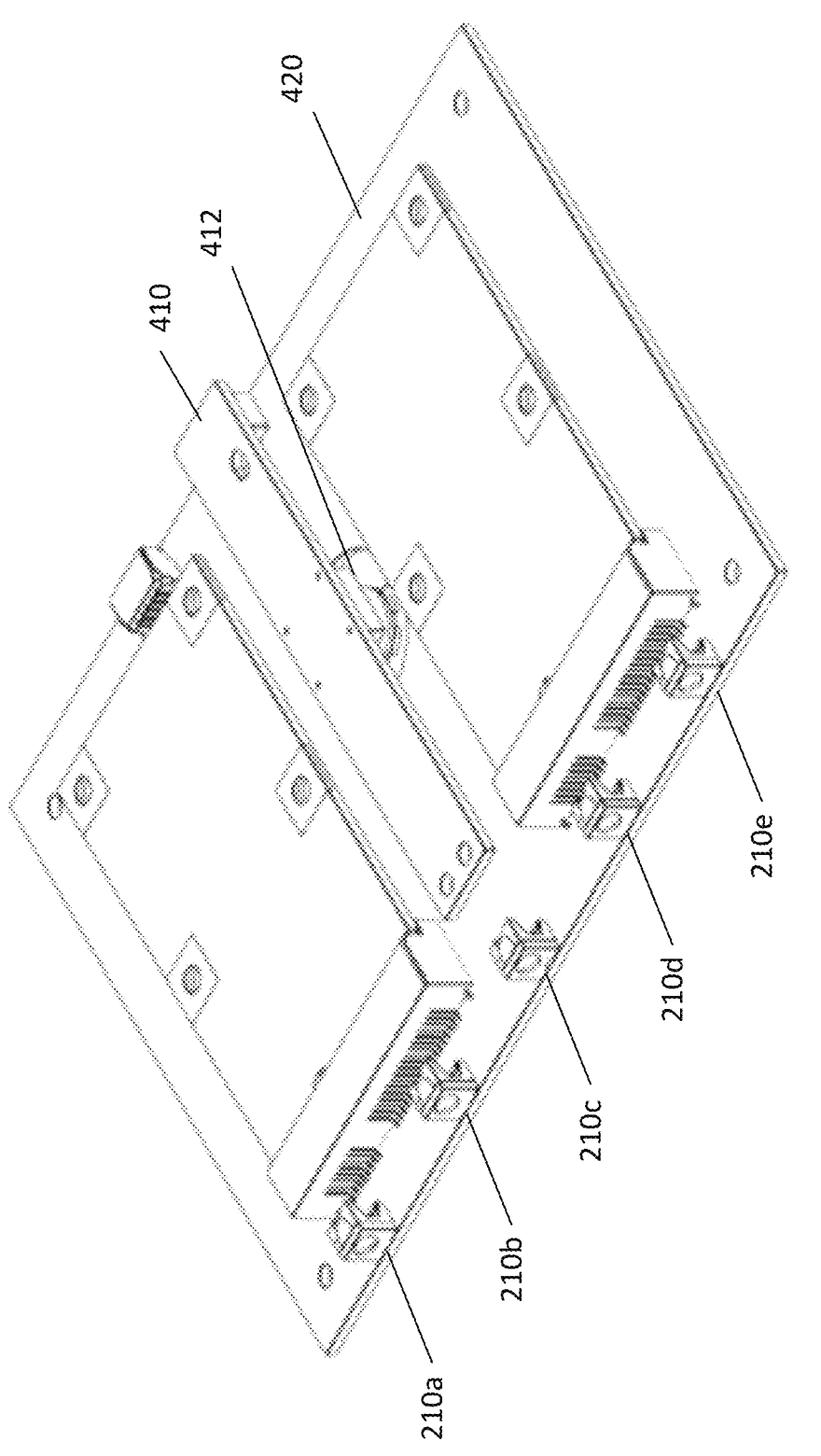
FIG. 4a depicts an orthogonal view of an LED testing and indicating board within the testing device according to an embodiment of the present invention.

FIG. 4*a* depicts an orthogonal view of an LED testing board 410 and indicating board 420 within the testing device 100 according to an embodiment of the present invention. The LED testing board 410 includes a plurality of LED's (not shown) to provide a variety of wavelengths of light that shine upon the LFA strip. The LED testing board 410 may include one or more UVC light sources (not shown) to sterilize the portion of the testing device 100 that comes in contact with the sample. The LED testing board 410 includes a camera to take an image of a barcode present on an assay tube and of any LFA strips inserted into the testing device 100. These images are then communicated to the on-board computer within the testing device 100. The LED testing board 410 resides on the indicating board 420 that supports the indicators previously described. A hole in the indicating board 420 allows for the camera 412 on the LED testing board 410 to view the LFA strip. The LED testing board may further include two or more probes to measure conductivity of the test line on the LFA strip. This conductivity is provided to the processor, described later, to be used in determining intensity as an input to the equivalence curve used to determine the equivalent, standardized result, e.g. in the case of COVID-19 an eCt result. The LED testing board also contains a temperature and a humidity sensor.

Figure 4B:
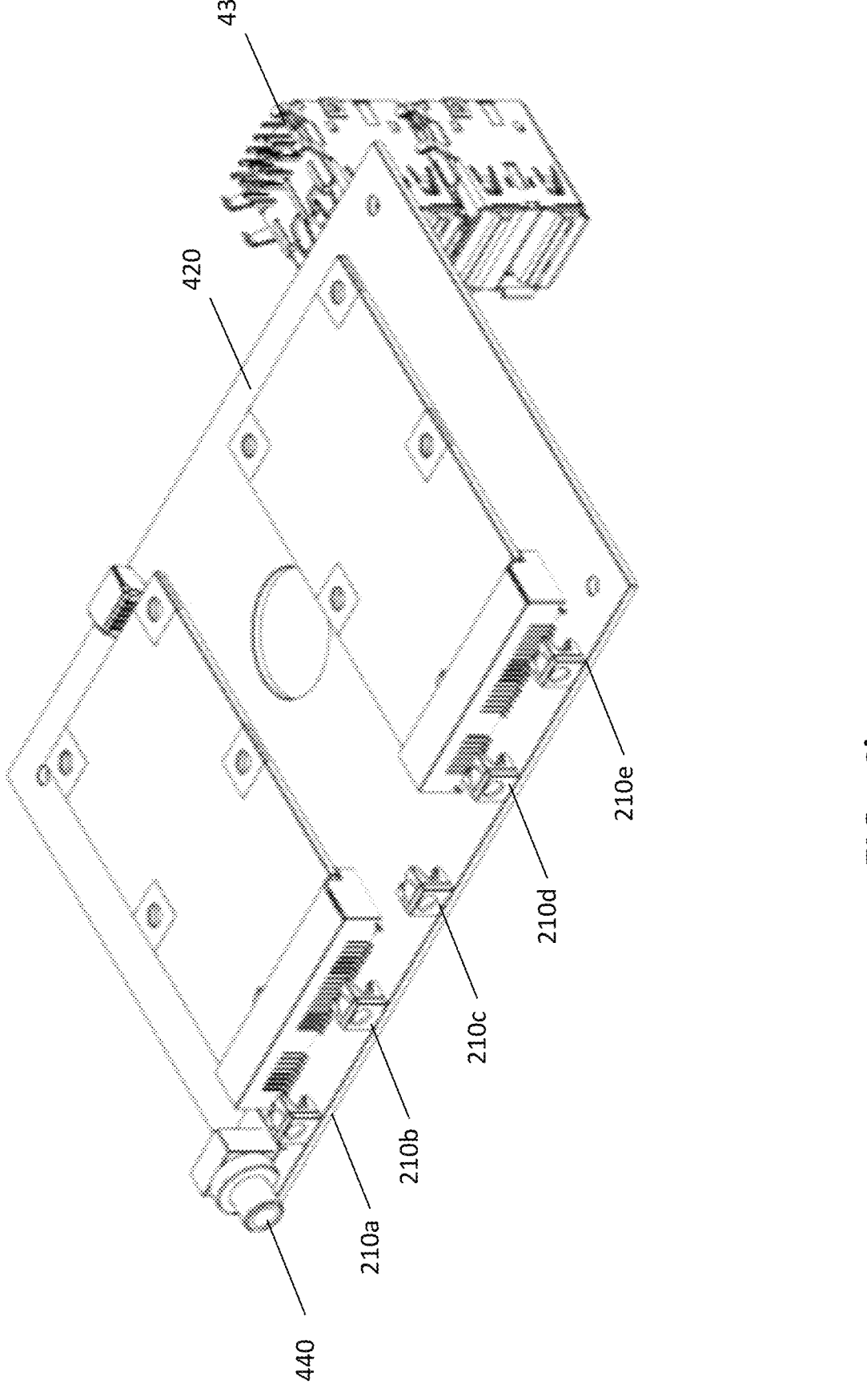
FIG. 4b depicts an orthogonal view of another embodiment of an indicating board within the testing device according to an embodiment of the present invention.

FIG. 4*b* depicts an orthogonal view of another exemplary embodiment of the indicating board 420 within the testing device 100 according to an embodiment of the present invention. A power switch 440 may be provided on the indicating board 420 to power the testing device 100 on and off. A multi-port USB connector 430 may be provided that allows a carrier, such as removable sample carrier 120, to have electronic features that communicate with a host PC and its software. The positioning of the USB connectors relative to the sample carriers are aligned such that a PCB mounted within the sample carrier can use edge gold fingers in the same position as a typical USB connector, thus eliminating the need for an actual USB connector to be mounted on the PCB, and the USB connection between the PCB and the USB connector 430 is made when the sample carrier is inserted.

Figure 5:
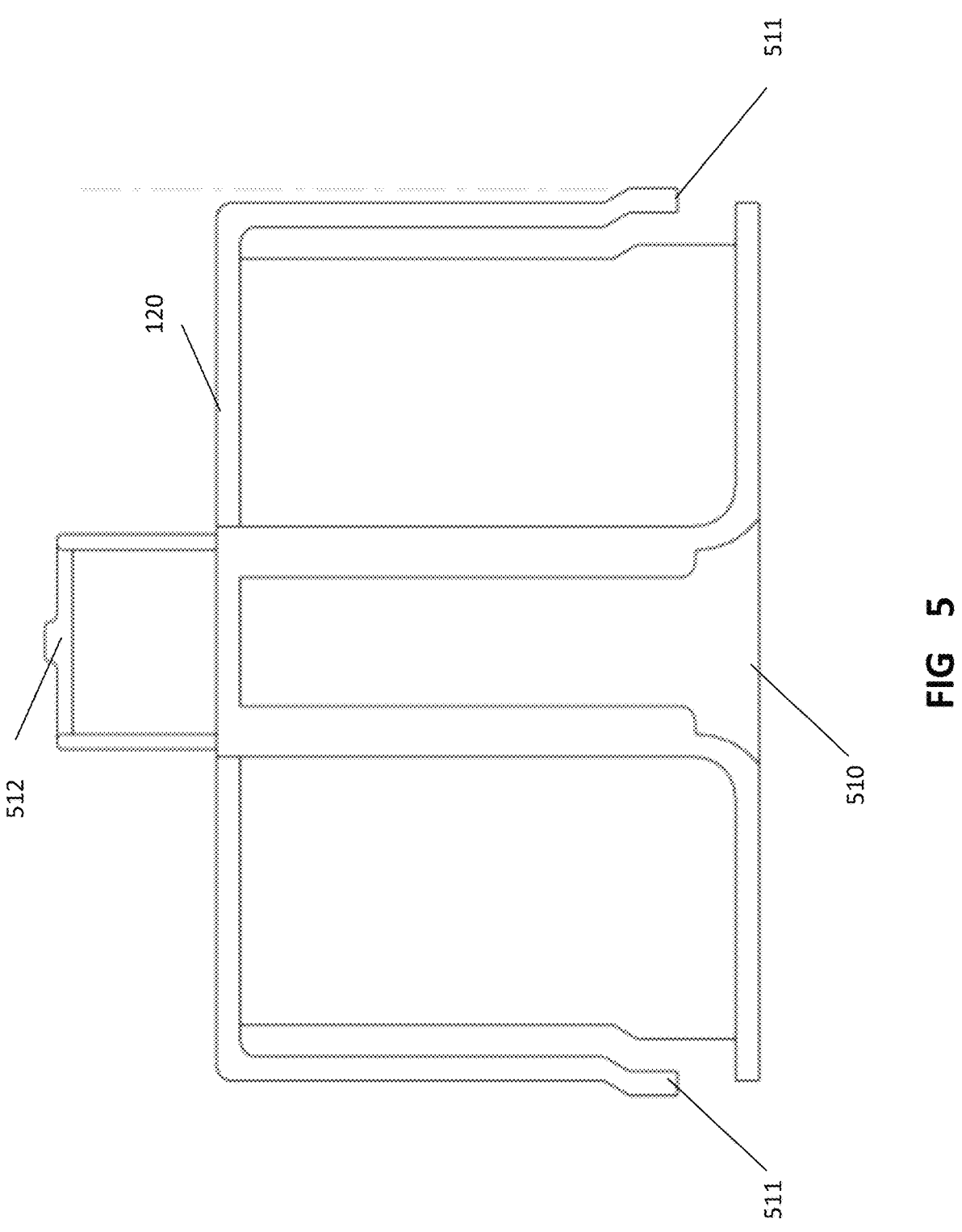
FIG. 5 depicts a top-down view of a sample carrier used in the testing device according to an embodiment of the present invention.

FIG. 5 depicts a top-down view of a removable sample carrier 120 used in the testing device according to an embodiment of the present invention. The removable sample carrier 120 receives an assay tube or carriage containing an LFA strip in opening 510 and supports it while camera 412 takes an image of the LFA strip. It is removable in an exemplary embodiment, so that as testing carriages or assay tubes change in the future, it may be swapped out. The removable sample carrier may include an active USB controller coupled to a mechanical switch or photo-optical device for sensing the presence of the assay tube or carriage. There are features on the sides 511 to latch with the chassis as the sample carrier is installed in the chassis, and a structure that serves like a spring 512 in the rear both holding the carrier in place during shipping and providing tension.

Figure 6A:
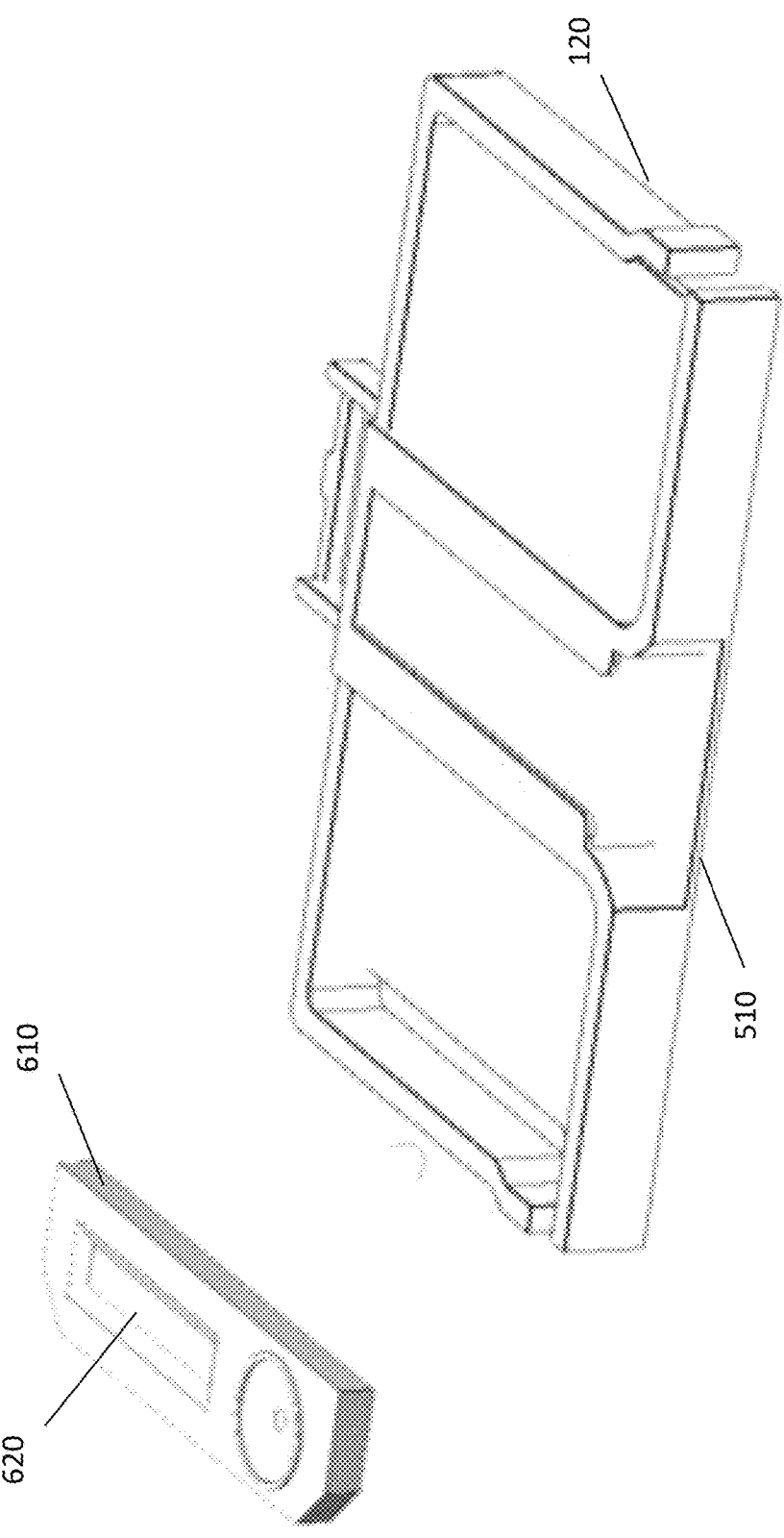
FIG. 6a depicts an orthogonal view of the sample carrier with a sample cassette used in the testing device according to an embodiment of the present invention.
Figure 6B:
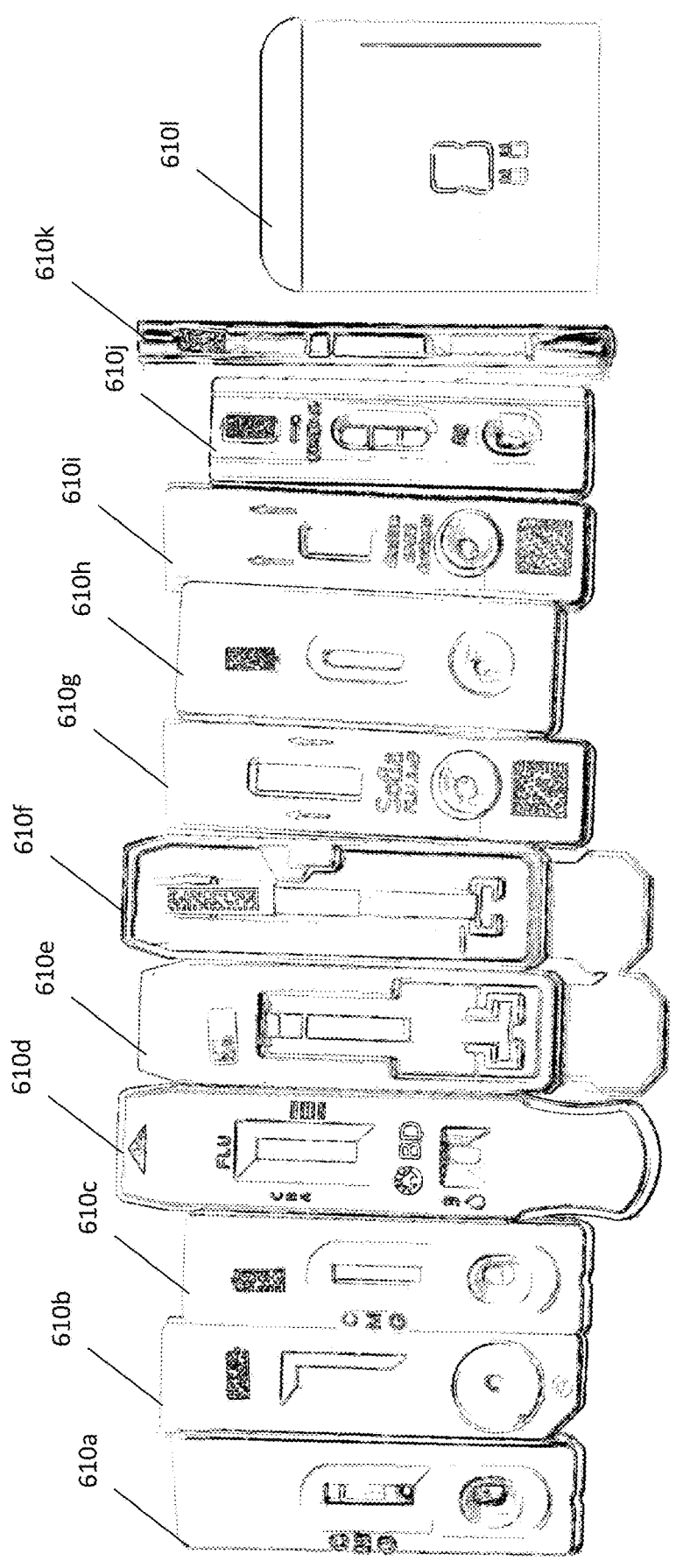
FIG. 6b depicts a plurality of cassettes that may be used in conjunction with the testing device according to an embodiment of the present invention.

FIG. 6*a* depicts an orthogonal view of the removable sample carrier 120 with a sample cassette 610 containing an LFA strip 620 used in the testing device 100 according to an embodiment of the present invention. FIG. 6*b* depicts a plurality of cassettes 610a-1 that may be used in conjunction with the testing device 100. Cassette 610k is a clear assay and cassette 6101 is a card containing an LFA test strip.

Figure 6C:
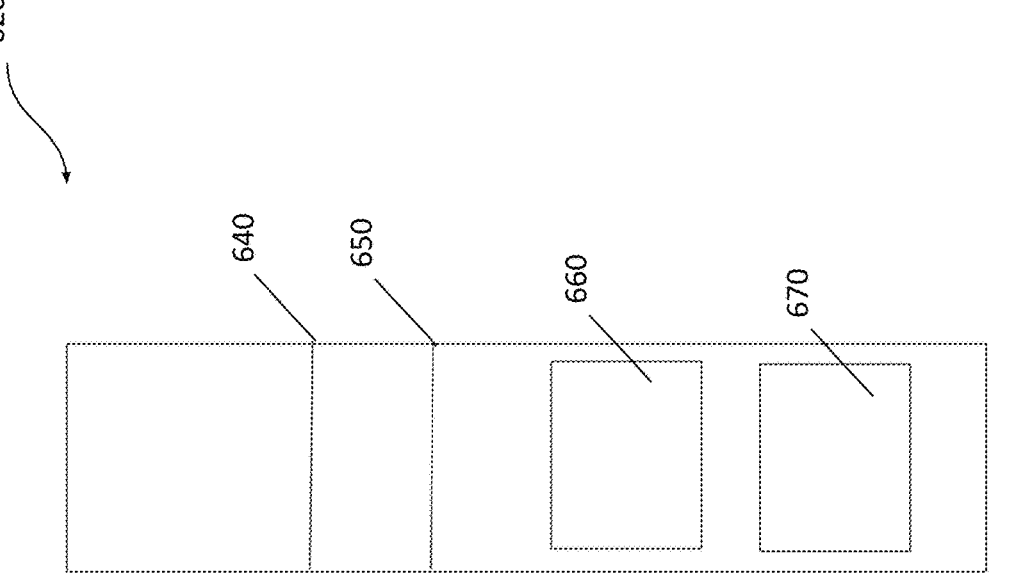
FIG. 6c depicts a lateral flow assay strip within the cassette according to an embodiment of the present invention.

FIG. 6*c* depicts the LFA strip 620 within the cassette 610 according to an embodiment of the present invention. The LFA strip 620 has at least one control line 640, test line 650, conjugate pad 660, and analyte pad 670. An analyte containing a sample from a domain is placed on the analyte pad 670. The analyte flows up the LFA strip 620 through the area of the strip having the conjugate pad 660, test line 650, and control line 640. Testing systems may be used in multiple domains. The domain, mentioned above, is the human domain, but testing is also performed in other domains, such as animals and the environment, for example. Reference to a domain herein is reference to any situation, for example, human testing, animal testing, environmental testing, and food testing.

The material of the test line 650 provides a positive result in the presence of a chemical-of-interest being tested for in the domain and a negative result in the absence of the chemical-of-interest being tested for in the domain. Where the chemical-of-interest can be a pathogen, or a piece of a pathogen, a biological marker, such as a protein of a chemical organic or inorganic, and where the biological marker can specifically be a substance such as the active ingredient in a drug, food additive, or environmental pollutant. The intensity of the test line 650 is measured by testing device 100, either visually or through the conductivity probes described earlier, in order to be used with the equivalence curve to determine an equivalent, standardized result, such as an eCt value.

Figure 7A:
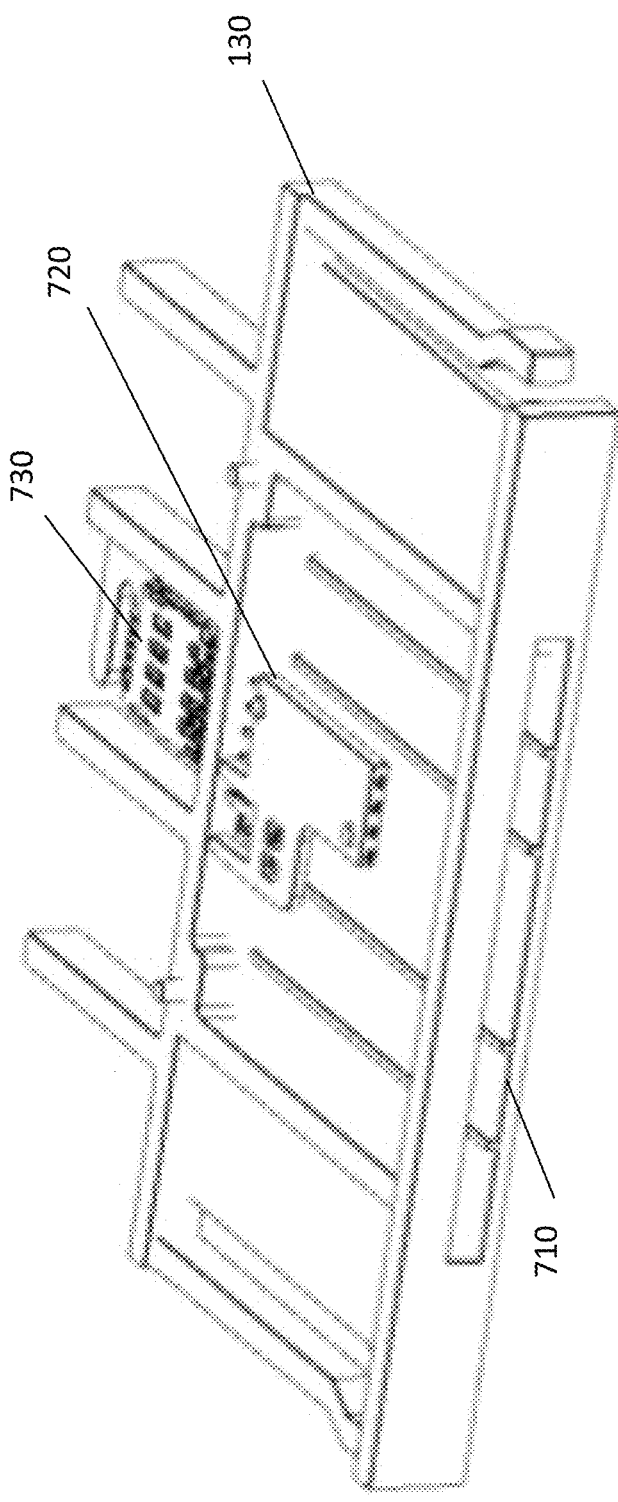
FIG. 7a depicts an orthogonal view of a card reader used in the testing device according to an embodiment of the present invention.
Figure 7B:
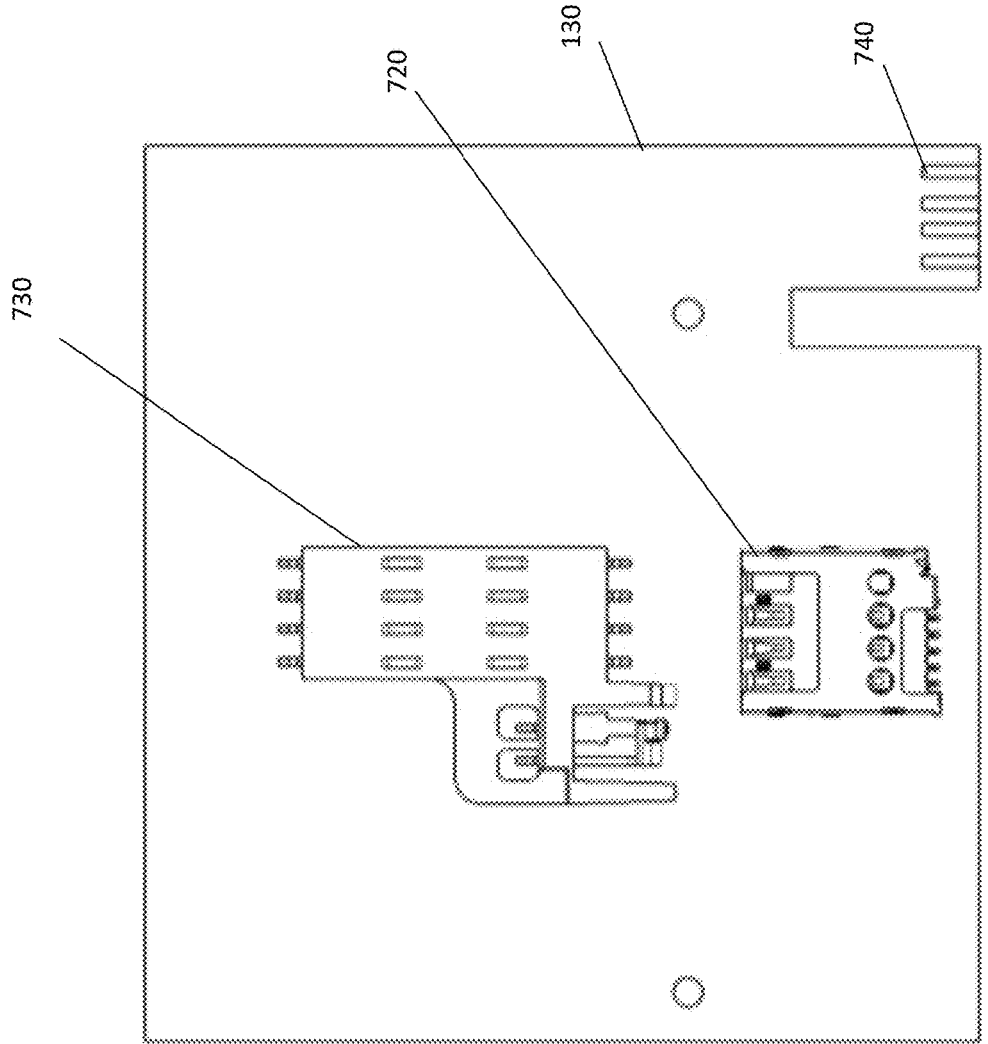
FIG. 7b depicts a top view of the card reader used in the testing device according to an embodiment of the present invention.

FIG. 7 depicts an orthogonal view of a removable card reader 130 used in the testing device 100 according to an embodiment of the present invention. As previously discussed, the card reader 130 receives a smart card, such as a credit card or national ID card, reads it with card reader 720 and provides the read information to the computer within the testing device 100. In alternative embodiments, the removable card reader 130 can read magnetic strips on credit cards or be modified for near field communication to read identifying information from a patient's mobile phone or tablet. In another alternative embodiment, an external reader may be used to read optical or near field communication information from patient identification, such as a passport. Identity collection accessories include the removable card reader 130 and the external reader.

Removable card reader 130 may have a secondary smart card reader 740 for inserting a smart card from a health care provider, such as a medical professional. For example in Taiwan doctors offices have smart card readers where patients can insert their cards, but the reader also requires a second smart card to be inserted by the doctor with their credentials for added security. The health care provider's smart card would be inserted into a second card or smart card slot 730 before the removable card reader 130 is inserted into the testing device 100.

The removable card reader 130 may have gold fingers to permit the removable card reader 130 to be plugged into the USB connector 340, without having to physically mate a printed circuit board in the removable card reader 130 with a computer system 800 (discussed with respect to FIG. 8 below). The removable card reader 130 may also be configured to receive the smart card upside down. This configuration would place the smart card reader 740 facing up on a floor of the removable card reader 130 and include a camera above the removable card reader 130 to read and communicate a signature from the smart card to the computer system 800.

In an alternative embodiment of the invention, instead of a card reader being separated from the sample carrier, the card reader and sample carrier are in the same reception tray, such that an identification card (such as a driver's license) and assay tube or carriage are inserted side-by-side. In this embodiment, two cameras above the reception tray may be used, where a first camera reads the assay tube or carriage and a second camera reads the identification card visually, such as by PDF-417. PDF417 is a stacked linear barcode format used in a variety of applications such as transport, identification cards, and inventory management. "PDF" stands for Portable Data File. The "417" signifies that each pattern in the code consists of 4 bars and spaces in a pattern that is 17 units (modules) long.

Figure 8:
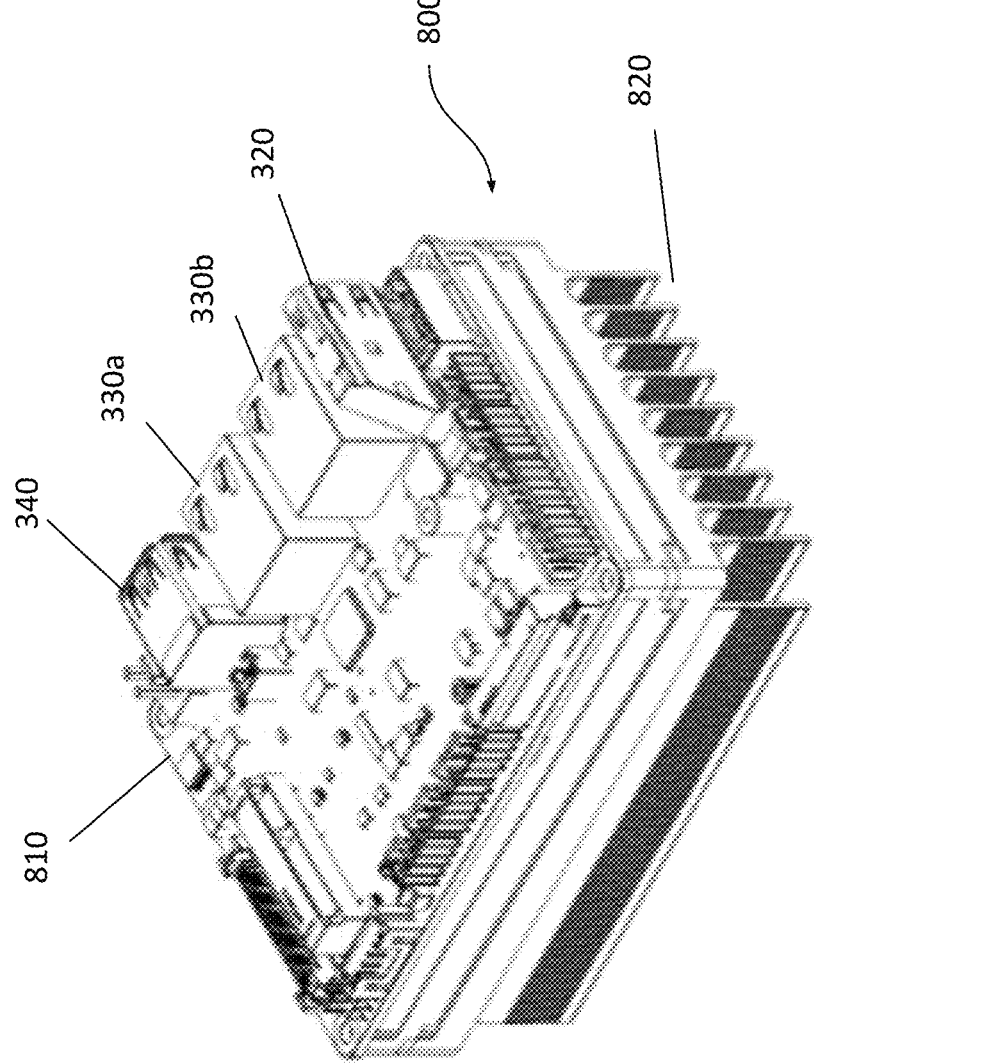
FIG. 8 depicts an orthogonal view of a computer used in the testing device according to an embodiment of the present invention.

FIG. 8 depicts an orthogonal view of a computer system 800 used in the testing device 100 according to an embodiment of the present invention. The computer system 800 will be described in more detail in FIG. 9, but includes a PC board or Motherboard 810, along with a heat sink 820. In an exemplary embodiment, the computer system 800 resides in the bottom of the testing device 100 and is physically separated from the removable sample carrier 120. The computer hosts the ports 320, 330, and 340 previously discussed.

Figure 9:
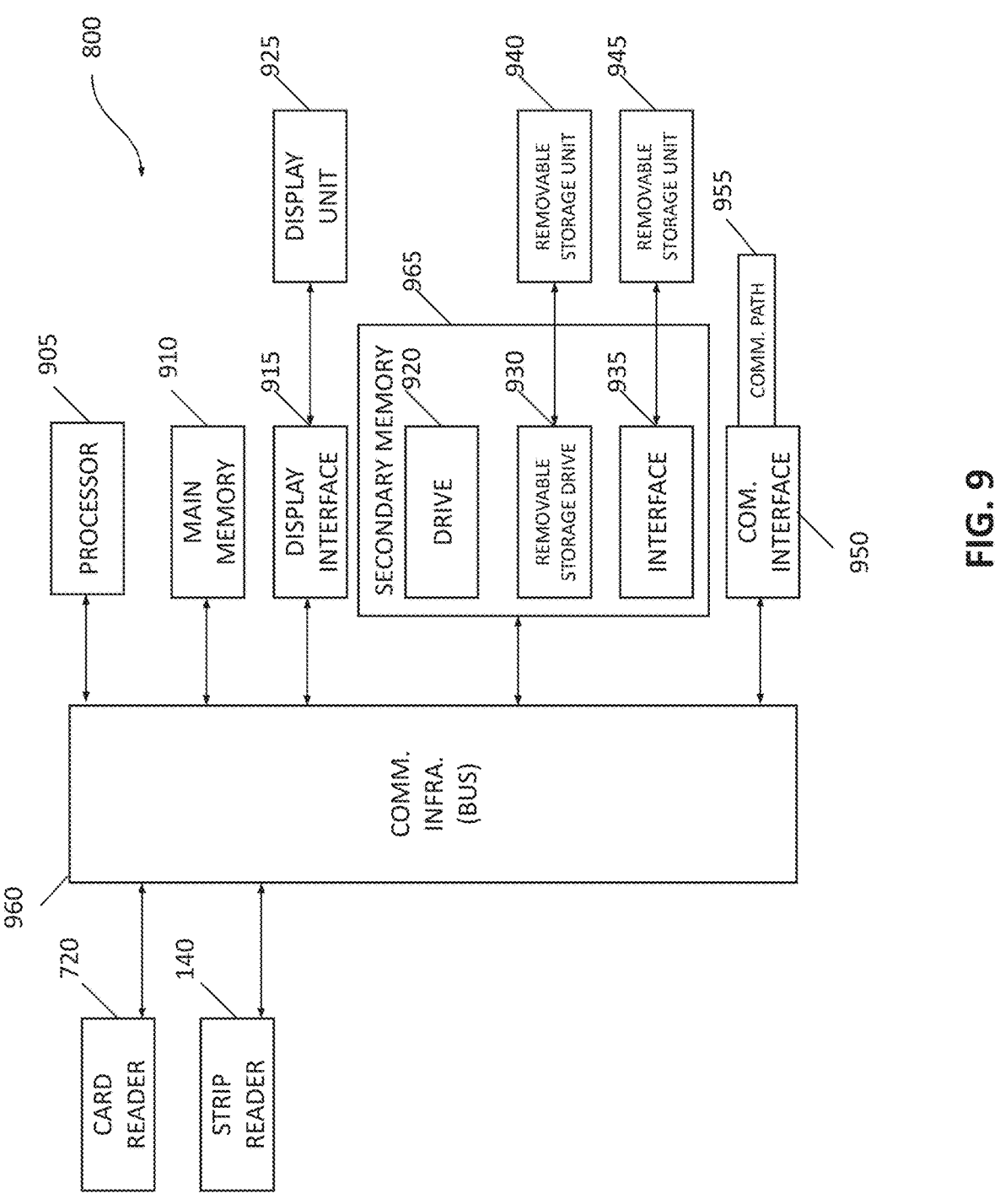
FIG. 9 depicts a block diagram of the computer used in the testing device according to an embodiment of the present invention.
Figure 15:
FIG. 15 depicts a flowchart for training a test strip reader in accordance with an embodiment of the present invention.
Figure 15:
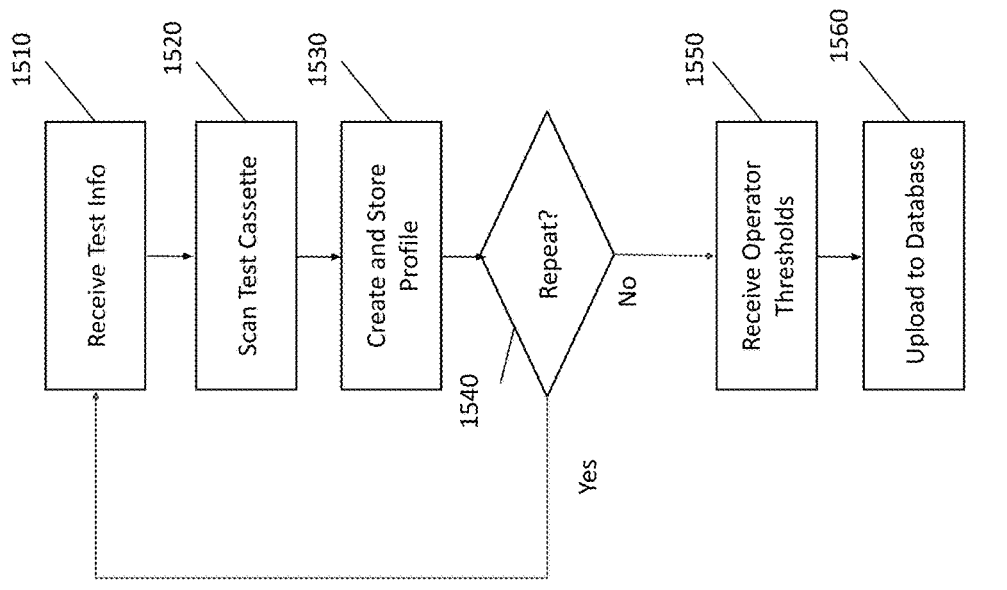

FIG. 9 depicts a block diagram of the computer system 800 used in the testing device according to an embodiment of the present invention. FIG. 9 depicts a high-level block diagram computer system 800, which can be used to implement one or more aspects of the present invention. More specifically, computer system 800 can be used to implement some hardware components of embodiments of the present invention. Although one exemplary computer system 800 is shown, those skilled in the art after reading this disclosure will understand that other implementations are also possible. Computer system 800 includes a communication path 955, which connects computer system 800 to additional systems (not depicted) and can include one or more wide area networks (WANs) and/or local area networks (LANs) such as the Internet, intranet(s), and/or wireless communication network(s). In one exemplary embodiment, communication path 955 includes wireless local area network communication, mobile or cellular wireless communication, and wired (such as Ethernet) communication. Computer system 800 is in communication via communication path 955, e.g., to communicate data between them. The computer system 800 may also contain an optional internal battery and battery charger that allows the unit to be charged. Alternatively an external battery with a power cord connected to the unit may be used, where the external battery unit features the same input connector as the computer system, and the external battery unit may then be installed in the field to provide robustness against power outages or to be used in the field where wall power is not available. An example of such a device is shown in FIG. 15.

Computer system 800 includes one or more processors, such as processor 905. Processor 905 is connected to a communication infrastructure 960 (e.g., a communications bus, cross-over bar, or network). Computer system 900 can include a display interface 915 that forwards graphics, text, and other data from communication infrastructure 960 (or from a frame buffer not shown) for display on a display unit 925. In a headless device, such as testing device 100, no display unit is present 925, although one may be added by connecting to HDMI port 320. Computer system 900 also includes a main memory 910, preferably random access memory (RAM), and can also include a secondary memory 965. Secondary memory 965 can include, for example, a hard disk or solid-state drive 920 and/or a removable storage drive 930, representing, for example, a floppy disk drive, a magnetic tape drive, or an optical disk drive. Removable storage drive 930 reads from and/or writes to a removable storage unit 940 in a manner well known to those having ordinary skill in the art. Removable storage unit 940 represents, for example, a floppy disk, a compact disc, a magnetic tape, solid state, or an optical disk, etc. which is read by and written to by removable storage drive 930. As will be appreciated, removable storage unit 940 includes a computer readable medium having stored therein computer software and/or data.

In alternative embodiments, secondary memory 965 can include other similar means for allowing computer programs or other instructions to be loaded into the computer system. Such means can include, for example, a removable storage unit 945 and an interface 935. Examples of such means can include a program package and package interface (such as that found in video game devices), a removable memory chip (such as an EPROM, or PROM) and associated socket, and other removable storage units 945 and interfaces 935 which allow software and data to be transferred from the removable storage unit 945 to computer system 800.

Computer system 800 can also include a communications interface 950. Communications interface 950 allows software and data to be transferred between the computer system and external devices. Examples of communications interface 950 can include a mobile modem using, for example, 3G, 4G/LTE, 5G, and future mobile standard networks, a network interface (such as an Ethernet card), a communications ADV0005 Page 17 of 41 port, or a PCI, Mini PCI, or PCIe slot and card, for example. Software and data transferred via communications interface 950 are in the form of signals which can be, for example, electronic, electromagnetic, optical, or other signals capable of being received by communications interface 950. These signals are provided to communications interface 950 via communication path (i.e., channel) 955. Communication path 955 carries signals and can be implemented using wire or cable, fiber optics, a phone line, a cellular or mobile phone link, an RF link, and/or other communications channels.

In the present description, the terms "computer program medium," "computer usable medium," and "computer readable medium" are used to generally refer to media such as main memory 910 and secondary memory 965, removable storage drive 930, and a hard disk installed in hard disk drive 920. It may also refer to flash storage options, such as USB thumb drives or SD cards. Computer programs (also called computer control logic) are stored in main memory 910 and/or secondary memory 965. Computer programs can also be received via communications interface 390. Such computer programs, when run, enable the computer system to perform the features of the present invention as discussed herein. In particular, the computer programs, when run, enable processor 905 to perform the features of the computer system. Accordingly, such computer programs represent controllers of the computer system.

Communication infrastructure 960 also communicates with card reader 720 for reading identification or credit/debit card information from a user or patient and a strip reader 140 for optically reading the results on a test strip.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 10:
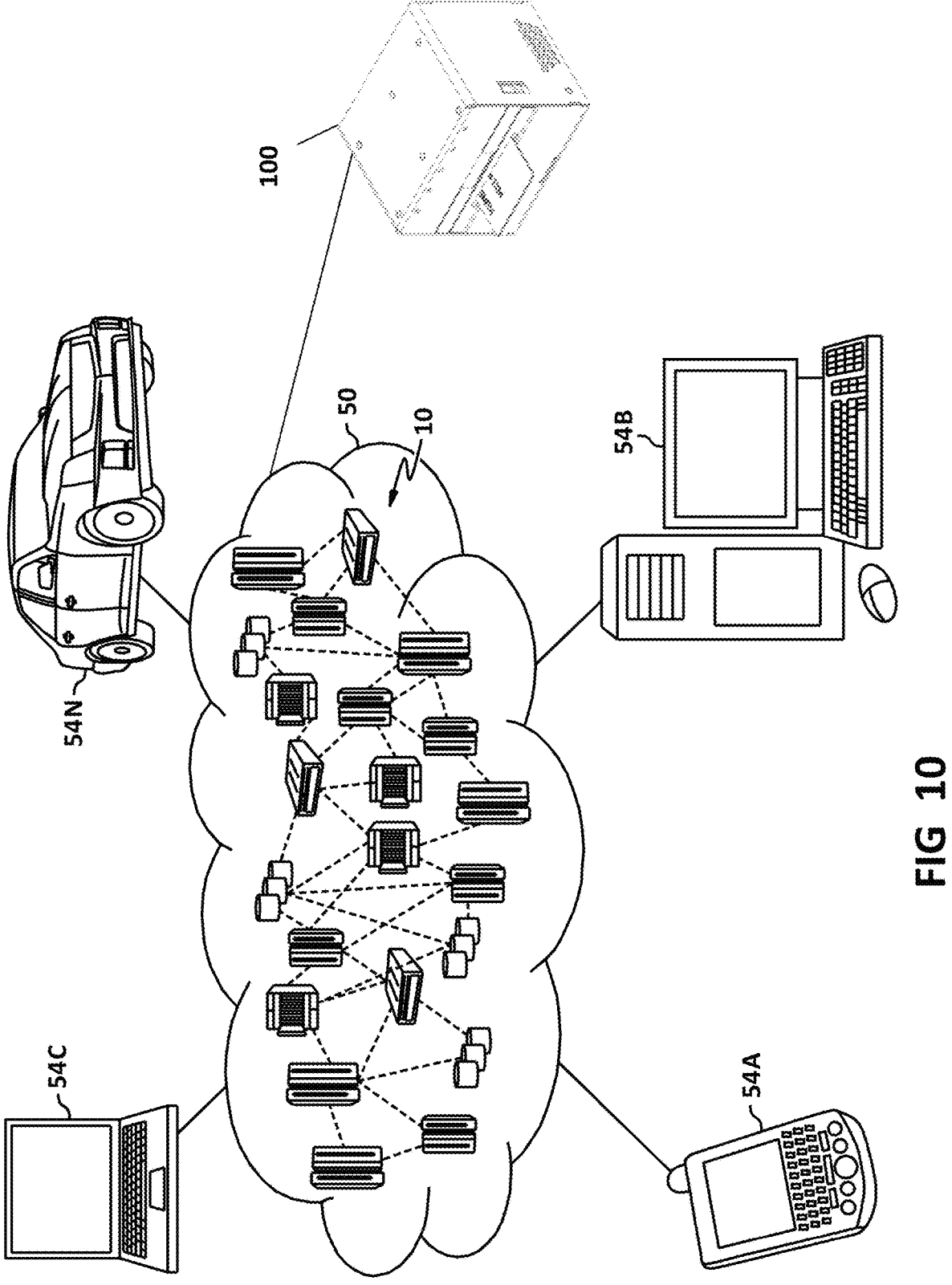
FIG. 10 depicts an environment for using a system in accordance with an embodiment of the present invention.

Referring now to FIG. 10, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, testing device 100 and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N and 100 shown in FIG. 1 are intended to be illustrative only and that computing nodes 10 and cloud computing environment 50 can communicate with any type of computerized device over any type of network and/or network addressable connection (e.g., using a web browser).

Figure 11:
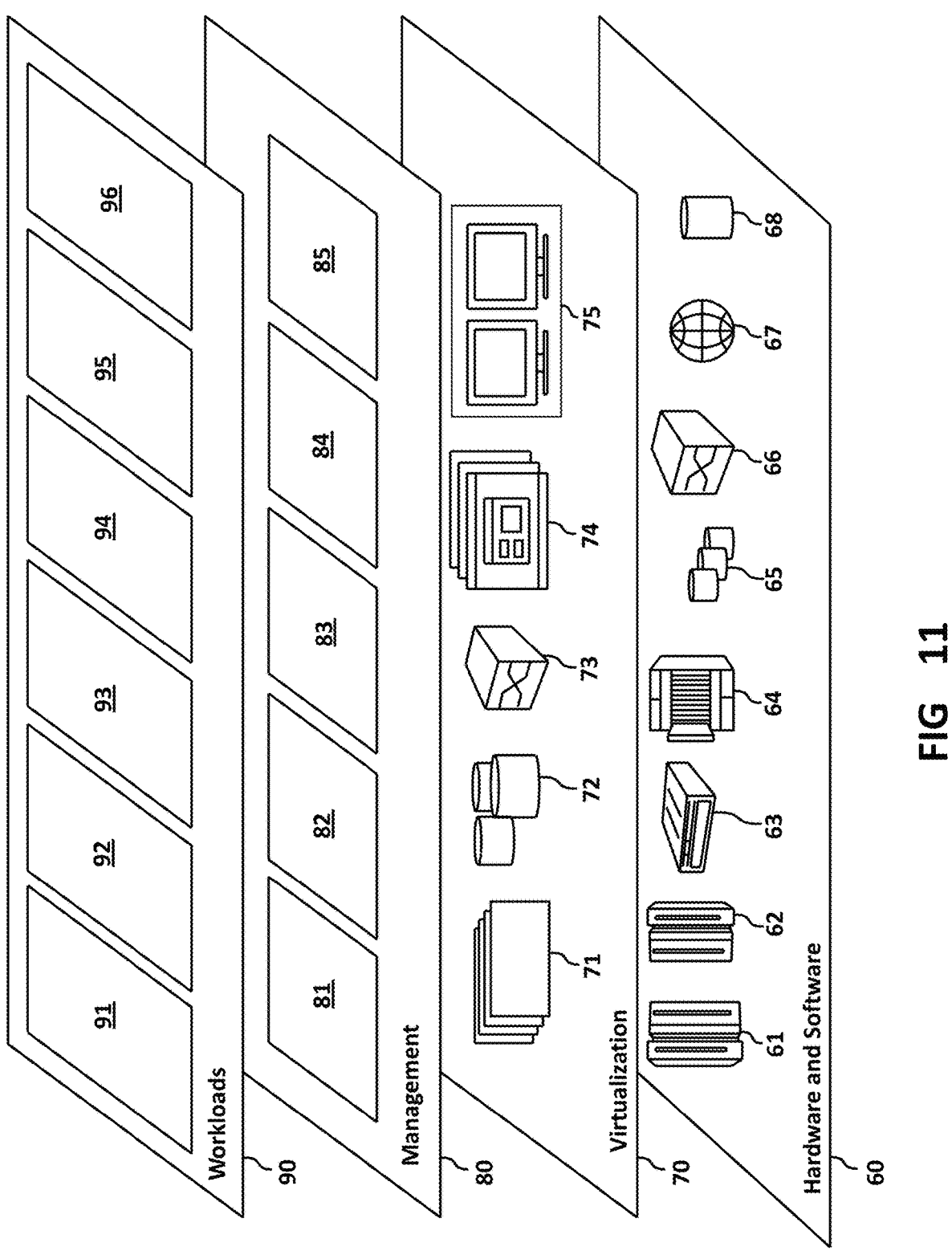
FIG. 11 depicts a high-level block diagram computer system, which can be used to implement one or more aspects of the present invention.

Referring now to FIG. 11, a set of functional abstraction layers provided by cloud computing environment 50 (FIG. 10) is shown. It should be understood in advance that the components, layers, and functions shown in FIG. 11 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65 storing test databases and results databases; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: data mining of test databases and results databases 91; software development and lifecycle management 92; machine learning of test strip analysis 93; headless testing device communications and control 94; computer (non-headless) communication and control 95; and testing analysis 96.

Figure 12:
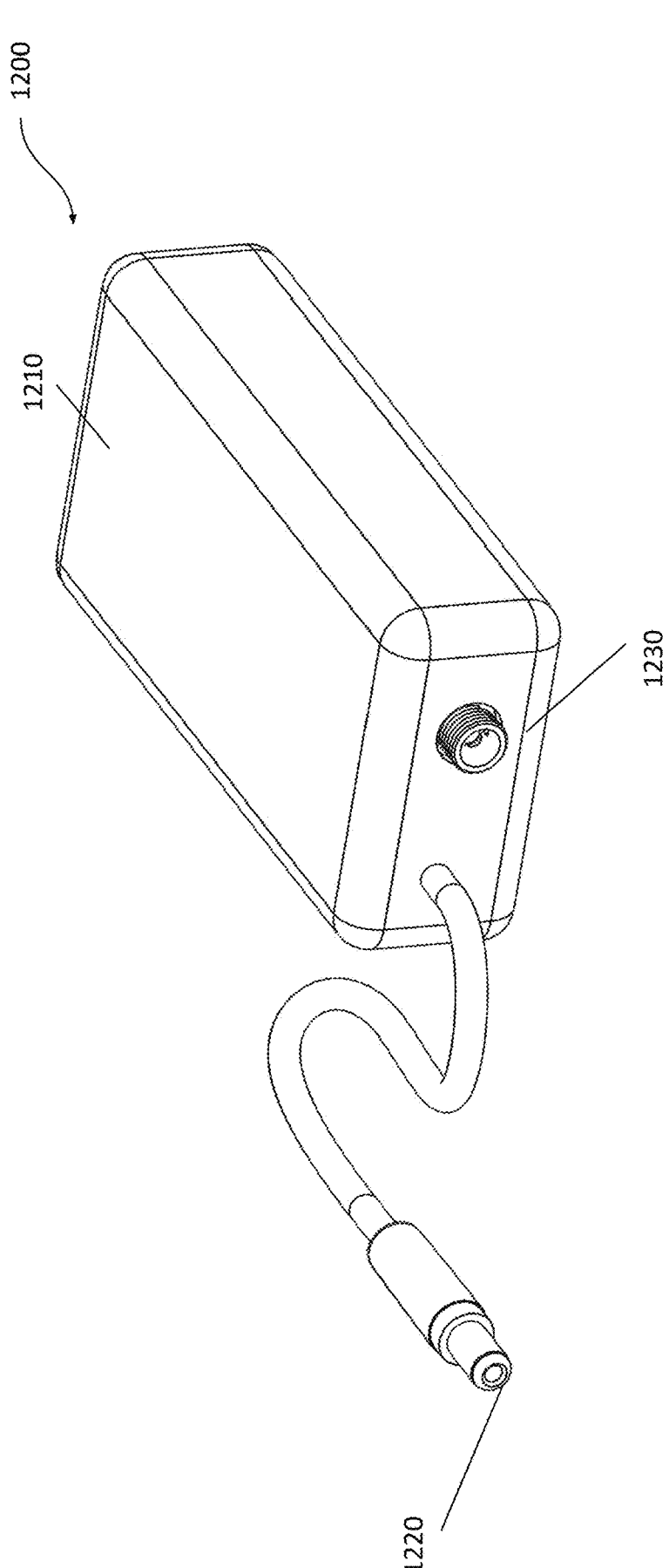
FIG. 12 depicts an orthogonal view of a battery pack for the testing device according to an embodiment of the present invention.

FIG. 12 depicts an orthogonal view of a battery pack 1200 for the testing device 100 according to an embodiment of the present invention. Battery pack 1200 includes an encased battery 1210 having a power input port 1230 for accepting a DC power supply and an output port 1220 for plugging in to a power input port of the testing device 100. By using battery pack 1200, testing device 100 may be used without needing an AC power source present.

14

Figure 13A:
FIG. 13a depicts a flowchart for generating an equivalence curve in accordance with an embodiment of the present invention.
Figure 13A:
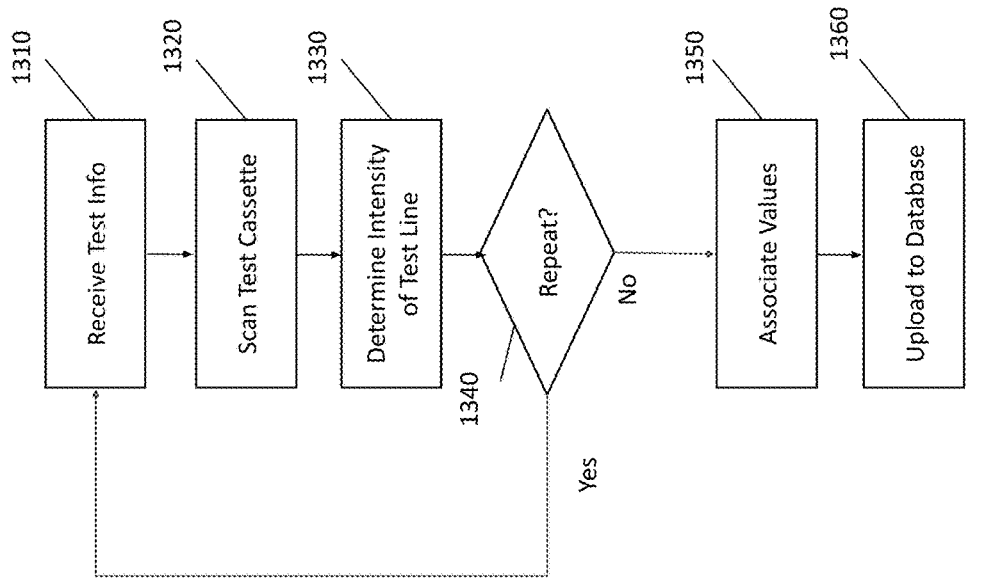

FIG. 13a depicts a flowchart 1300 for generating an equivalence curve in accordance with an embodiment of the present invention. Many different cassettes may be used in conjunction with testing device 100. For each cassette, it is desirable to not only be able to provide a positive or negative test result, but also to read the intensity of a testing line on the LFA strip and learn what level of response and color of line for a test corresponds to a level of antigen or antibody response. For COVID-19 testing, the intensity of the testing line correlates to a Ct level in order to later produce an equivalent Ct, or eCt, for a given intensity level for a given test line on the LFA strip. Again, intensity may be measured by a visual examination or an examination of the conductivity of a line where the conductivity of a line is proportional to viral load present on the LFA strip.

Therefore, a training method builds an equivalence curve for each type of cassette in conjunction with an operator. The operator prepares and uses known concentrations of specimens while taking an image of the cassette with that concentration while observing the image taken on a screen or reading an intensity level based on conductance. First, test information is received (block 1310). Test information includes, for example, the vendor of the test, type of test, and a number of control lines and test lines. The test cassette is scanned (block 1320) and a plurality of images are taken of the cassette or a conductance of the test line measured. When taking the images, the operator may adjust the light setting, such as a level of LED RGB light from, for example, 0% to 100%, for each color Red, Green, and Blue, as well as various ultraviolet light wavelengths from 200 nm up to 350 nm in increments of 10 nm, for example. All LEDs may not be needed for any particular test. An infrared LED may also be similarly used and adjusted.

For each given known concentration, an intensity of the test line is determined based on the plurality of images received from the scan (block 1330). This is described in more detail in FIG. 13b. The process may be repeated for additional cassettes with different concentrations but of the same type (block 1340), with those additional results saved in an equivalence curve for that test. The method associates the known concentration for that test, the standardized result, e.g., eCt for COVID-19 determined by running a PCR test on the known concentration and finding the Ct, and the determined intensity of the test line (block 1350). That information is stored in the equivalence curve.

For example, an exemplary test kit may have instructions for use ("IFU") that outlines the limit of detection at 2 ng/ml and an upper limit of 30 ng/ml. For that exemplary test kit, 2 ng/ml is placed on a test cassette, the operator waits a time specified in the IFU, a plurality of images are taken, and the determined intensity, e.g., 2.50, is stored as part of the equivalence curve. Alongside that, a 2 ng/ml sample is analyzed with PCR, and the Ct that results is stored and associated with the 2 ng/ml reading from the exemplary test kit. In addition, for that exemplary test kit, 30 ng/ml is placed on a test cassette, the operator waits the time specified in the IFU, a plurality of images are taken, and the determined intensity, e.g. 200, is stored. Alongside that, a 30 ng/ml sample is analyzed with PCR and the Ct that results is stored and associated with the 30 ng/ml reading from the exemplary test kit.

In most cases, the limit of detection of the exemplary cassette in a COVID-19 test will be associated with a Ct value of 35 and the upper limit of the exemplary cassette in a COVID-19 test will be associated with a Ct value of 15. Typically, values below 15 are not returned in PCR testing and are not valid. Thus, 15 is the upper threshold limit of detection. Values greater than 35 are indicative of a negative test and are not returned in PCR testing, and 35 is the lower threshold limit of detection.

When the operator is satisfied that the equivalence curve is complete across a range of equivalent results, the equivalence curve for that testing kit is uploaded to a central test database (block 1360). Thus a set of data points, having as an X parameter the measured intensity of the test line and as a Y parameter the standardized output, e.g., eCt, is stored as the equivalence curve in the central test database.

Figure 13B:
FIG. 13b depicts a flowchart for determining intensity of a test line in accordance with an embodiment of the present invention.
Figure 13B:
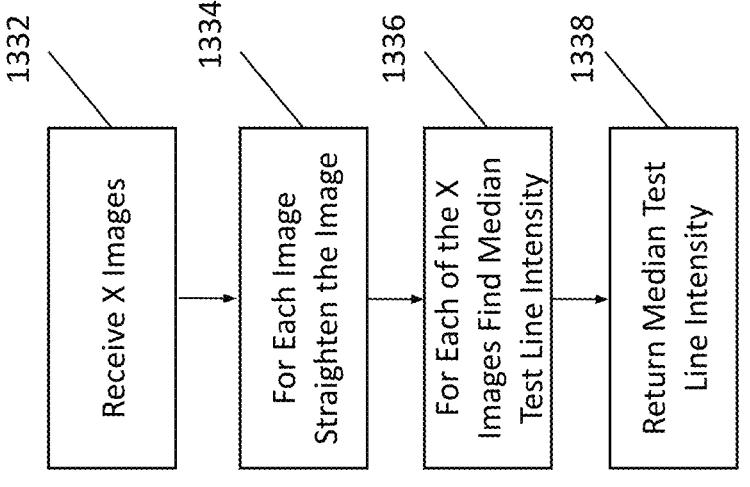

FIG. 13b depicts a flowchart for determining intensity of a test line 1330 in accordance with an embodiment of the present invention. A plurality of x images is received, where x is equal to or greater than one (block 1332). In an exemplary embodiment, x is equal to 10. Each of the x images is straightened, as carriers can be inserted askew, the area around the test line is selected (block 1334). Please note that the intensity values of 0-255 are inverted in that pure white is 0 and pure black is 255. A rectangular area around the test line is found for each of the x images, and typically may be between 3 and 10 pixels width of lines depending on the test kit manufacturer. Each column that comprises the test line is normalized to account for lighting and paper differences that may arise due to lighting variation and paper variation. The maximum median value of an intensity of the pixels in each line of the rectangular area comprising the test line is then determined for each of the x images, and then the median of the maximum median for each of the x images is returned (block 1336). This value is returned as the test line intensity (block 1338).

Figure 14:
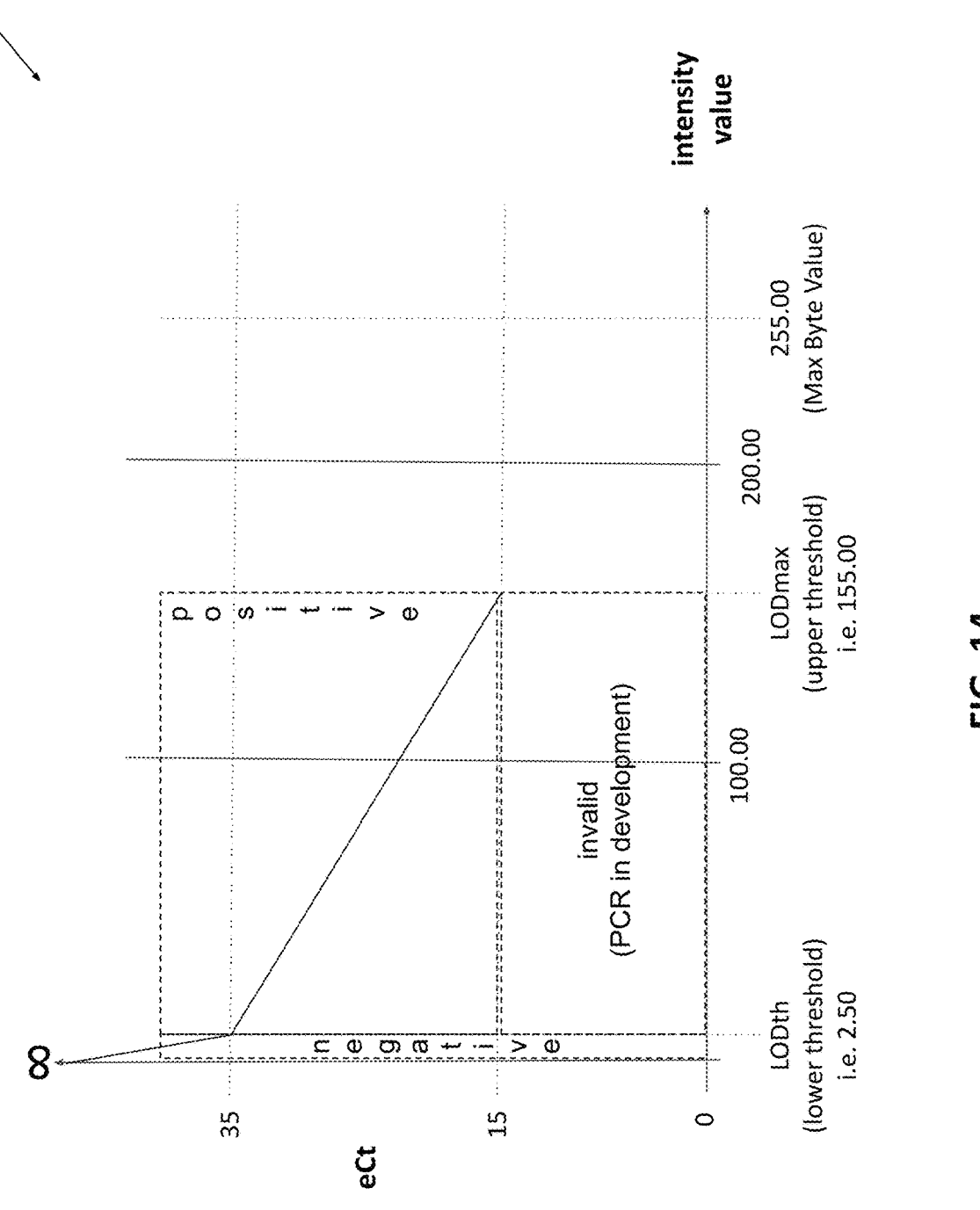
FIG. 14 depicts an equivalence curve in accordance with an embodiment of the present invention.

FIG. 14 depicts an exemplary equivalence curve 1400 in accordance with an embodiment of the present invention. This curve is a straight line regression curve generated as described above with only two points on the equivalence curve 1400: the limit of detection point with an eCt of 35 and the upper limit point with a Ct value of 15. The eCt of 35 corresponds to an intensity level of, for example, 2.50 in an intensity range of 0-255 corresponding in the example to 2ng/ml; the eCt of 15 corresponds to an intensity level of 155.00 in an intensity range of 0-255 corresponding in our example to 30 ng/ml. Points between are extrapolated during analysis of actual patient samples to generate an equivalent Ct or eCt. In this example, intensity values below 2.50 indicate a negative test, with values above that being positive.

As previously mentioned, and shown in the figure, in most cases, the limit of detection of the exemplary cassette in a COVID-19 test will be associated with a Ct value of 35 and the upper limit of the exemplary cassette in a COVID-19 test will be associated with a Ct value of 15. Typically, values below 15 are not returned in PCR testing and are not valid. Thus, 15 is the upper threshold limit of detection. Values greater than 35 are indicative of a negative test and are not returned in PCR testing, and 35 is the lower threshold limit of detection.

FIG. 15 depicts a flowchart 1500 for training a test strip reader in accordance with an embodiment of the present invention. Many different cassettes may be used in conjunction with testing device 100. For each cassette, it is desirable to not only be able to provide a positive or negative test result, but also to read the quality of a testing line on the LFA strip and learn what level of response and color of line for a test corresponds to a level of antigen or antibody response. Therefore, a training method builds a configuration profile for each type of cassette in conjunction with an operator. The operator prepares and uses known concentrations of specimens while taking an image of the cassette with that concentration while observing the image taken on a screen. First, test information is received (block 1510). Test information includes, for example, the vendor of the test, type of test, and a number of control lines and test lines. The test cassette is scanned (block 1520) and an image taken of the cassette. A profile is created and stored based on the image and operator input (block 1530). The operator may adjust the light setting, such as a level of LED RGB light from, for example, 0% to 100%, for each color Red, Green, and Blue, as well as various ultraviolet light wavelengths from 200 nm up to 350 nm in increments of 10 nm, for example. All LEDs may not be needed for any particular test. An infrared LED may also be similarly used and adjusted.

When the operator determines that an acceptable LED collar and level combination for a given test has been determined, the configuration profile for that test is stored. The configuration profile that is stored includes, for example, test name, data, time, vendor, type of test, number and types of control lines and test lines, LED values for the acceptable reading results, and an image of the test that produced the stored results.

The process may be repeated for additional cassettes with different concentrations but of the same type (block 1540), with those additional results saved in the configuration profile for that test. The operator determines what thresholds will be set for positive and negative tests, along with parameters that indicate an invalid test, such as a missing control line, missing bard code, or expired date of test, for example (block 1550). That information is also stored in the configuration file. When the operator is satisfied that the configuration file is complete, the configuration file is uploaded to a central test database (block 1560).

Figure 16:
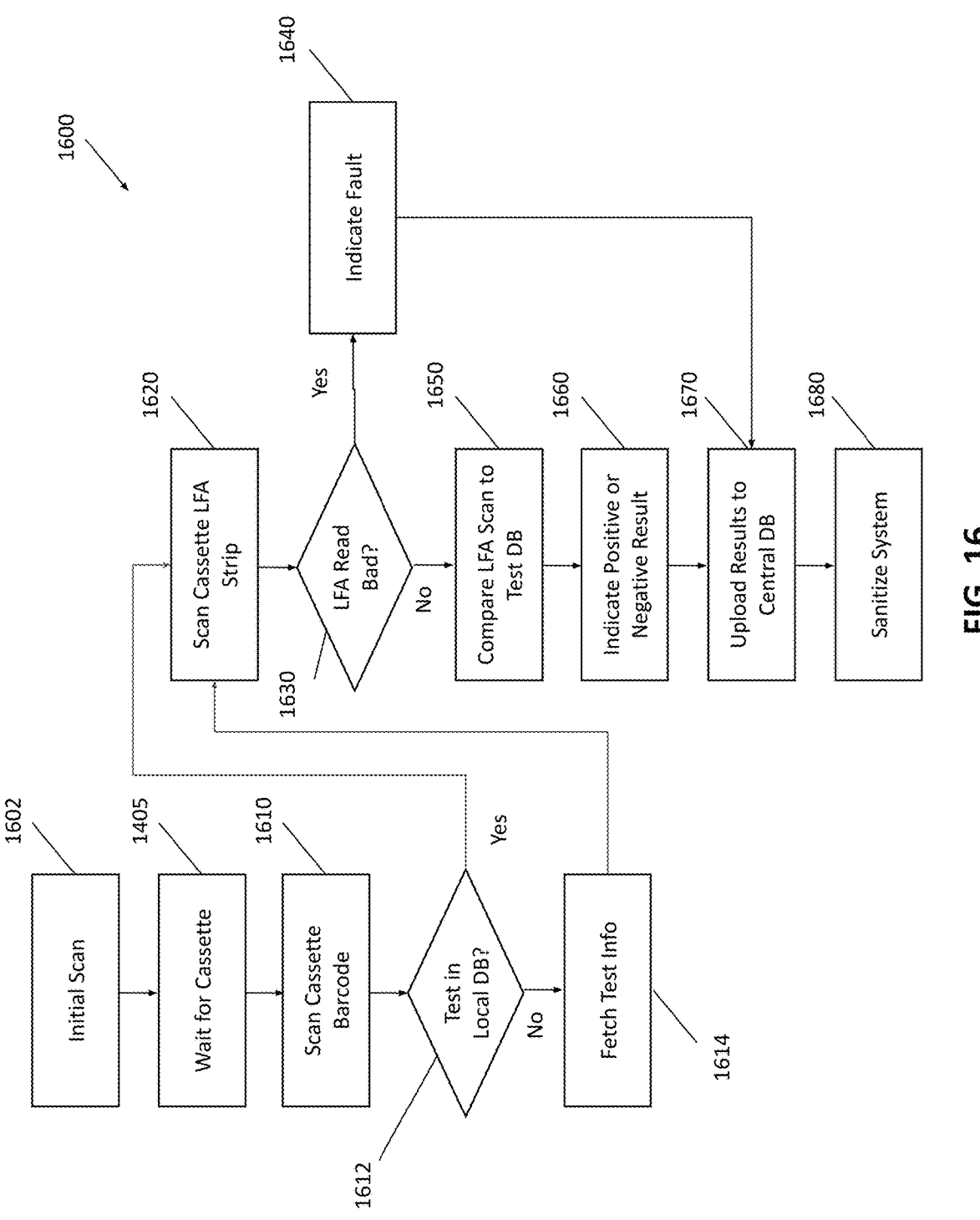
FIG. 16 depicts a flowchart of a method for reading a test strip in a clear assay or sample carrier and providing an standardized result, such as an equivalent Ct or eCt, in accordance with an embodiment of the present invention.

FIG. 16 depicts a flowchart 1300 of a method for reading a test strip in a clear assay or sample carrier and providing a standardized result, such as an equivalent Ct or eCt, in accordance with an embodiment of the present invention. The method may perform an initial scan where an inserted cassette, clear assay or card is scanned for quality defects and association with a patient (block 1602). This block is explained in more detail in FIG. 17. The method waits for the detection of a clear assay, cassette, or card (block 1605). The method uses an imaging source, such as, for example, a camera, data file or files, xerography device, video feed, data stream, or other source of image information, to detect visual features, such a visual feature may be the shape of the inserted cassette, text on the cassette, presence or absence of one or more barcodes, data matrices or QR codes, or one or more colors present on the cassette, for example. In an alternative embodiment, the method may use a mechanical switch to detect the presence of a clear assay, cassette, or card. If there is no clear assay, cassette, or card, the method waits in a loop that may be, for example, 1 second long, until the detection of the clear assay, cassette, or card.

The method scans a visual feature off of the clear assay, cassette, or card to identify a test that is being conducted and optionally a patient (block 1610). Any reference to cassette herein also incorporates the use of a clear assay. Embodiments of the invention may use a visual feature, such as text, a shape of the cassette, or identifiers of the cassette to determine the test being conducted. A visual feature may also be a barcode, QR code, or data matrix. For example, a COVID test may be being performed, but other tests as previously described, such as a seasonal flu test may be being performed. The method uses the visual feature to determine the test being conducted regardless of the alignment of the cassette with respect to the carrier. Alignment may include orientation of the cassette. In other words, regardless of orientation or alignment of the cassette, the visual feature is analyzed to determine the test being conducted.

In the case of a data matrix as the visual feature, information within the data matrix identifies a unique cassette identifier, a manufacturer code definition, supplier code definition, a profile code that together determine a test configuration profile to be used for this test. For other visual features, such as QR code, barcode, text, a shape of the cassette, identifiers of the cassette, or combinations thereof, in determining the test being conducted, the visual feature may initially be used to identify the test vendor. Once the test vendor is identified, if necessary, the specific test from that vendor is determined. Following identification of the vendor and specific test, the test configuration profile is determined.

A check is made to determine if the test configuration profile and equivalence curve is present in a local database (block 1612). Test configuration profiles and equivalence curves are stored locally in, for example, an XML file. Each XML file may contain multiple test configuration profiles with associated equivalence curves. If the test configuration profile or equivalence curve is not present in the local database, a fetch is made to pull the appropriate configuration file and equivalence curve from a central test database for storage in the local database (block 1614). Thus, new tests that are used in the field will cause the local database to update itself with information from the remote database.

The LFA strip is scanned by an imaging source (block 1620). The imaging source is, for example, a camera, data file or files, xerography device, video feed, data stream, or other source of image information. To scan the LFA strip, the configuration file corresponding to the profile number provides brightness settings for LEDs that provide light at various wavelengths that will shine upon the LFA strip. The LEDs are turned on to that appropriate brightness level, and after a delay to permit the LEDs to arrive at the proper brightness and a camera to stabilize to take an image at that brightness level, images are taken by the camera. The number of images taken is indicated by the configuration file associated with the configuration profile. The areas of the LFA strip indicated by the profile to contain control and test lines are analyzed for color and intensity and results are averaged between several images taken to determine numerical values to be presented as results of the LFA strip scan. In an alternative embodiment, probes are placed on the LFA strip at the test line to determine conductivity of the test line.

Intensity of the test lines and control lines are calculated as follows. Each of the plurality of images is straightened as carriers can be inserted askew, the area around the test lines and control lines is selected, and the intensity of the image is intensity normalized so that the blank part of the paper is set to zero (block 1334). Please note that the intensity values of 0-255 are inverted in that pure white is 0 and pure black is 255. The rectangular area of both the test lines and the control lines are found, and typically may be between 3 and 10 pixels width of lines depending on the test kit manufacturer. The median intensity lines within the lines are then averaged together by summing the intensity values of each pixel comprising both median lines and averaging the pixel intensity to determine an intensity of each of the test lines and control lines.

If the scan of the LFA strip is bad for any reason (block 1630), an invalid result is indicated (block 1640) and the result indicating a fault may be uploaded to a central database in association with the patient's unique ID (block 1670). If the scan of the LFA strip is good, the LFA scan is compared to the associated test configuration profile to determine an LFA test result (block 1650). The actual value data of each test is stored and sent back to the central patient database so that a graph can be plotted for tests taken of a patient over time to see the magnitude of viral load or antibody concentration over time. Also, mathematical models may be used to develop data across large data sets of patients to see for example efficacy of a vaccine as a function of IgG/IgM concentration from samples taken over time across a cohort of patients. Patient information that identifies a specific person, such as a social security number or national ID number, may optionally not be stored in the central patient database, with only demographic data retained.

The numerical values from the LFA strip scan are used as input to an algorithm that uses concentration versus intensity data stored in the configuration profile to calculate a test result. The test result is an intensity value. The intensity value is used in conjunction with the equivalence curve previously determined for that test kit to determine a standardized test result value, such an equivalent Ct (or eCt) in the case of a COVID-19 test.

The following may be stored as a test result collection instance: standardized test result value, for example, eCt; one or more images of the actual LFA test strip used for the analysis; read values for the test and control lines; the test result, i.e., positive, negative, or invalid, according to the profile; the date, time, and GPS location of the test; serial number of the test from the bar code, QR code, or data matrix of the cassette or clear assay; serial number of the machine used for the test; operator code; and patient ID, drivers license number, ID number, health record numbers from a smart card reader or as read by the camera.

The test results, positive or negative, are provided to the patient via indicators on the testing device 100 (block 1660) and results as described above of the test may be uploaded to a central patient database in association with the patient's unique ID (block 1670). Regardless of test results, positive, negative, or invalid, the testing device is sanitized (block 1680). In addition, the method may account for privacy regulations or laws by periodically purging test information from the local database.

The barcode or datamatrix contains several digits that serve as an index into a configuration file, where the digits are interpreted as a profile code and provides the system information about the specific test that has been inserted into the machine. Based on this profile, the test device 100 configures the LED color; the combination of visual vs ultraviolet LEDs; where, what type of, and how many test lines a test strip has; and which intensity of a testing line corresponds to the size of a viral load. This enables accurate qualitative reading of values rather than just positive or negative values based on a threshold. If the Profile Code read is not found in the configuration file, the system will reach out and fetch an updated configuration file from a known network location, thus enabling for new types of tests to be released into the market and into the test devices 100 installed in the field, updating based on demand rather than having to push an update to test devices 100 in the field, which may or may not be on or in use at any given time.

Figure 17:
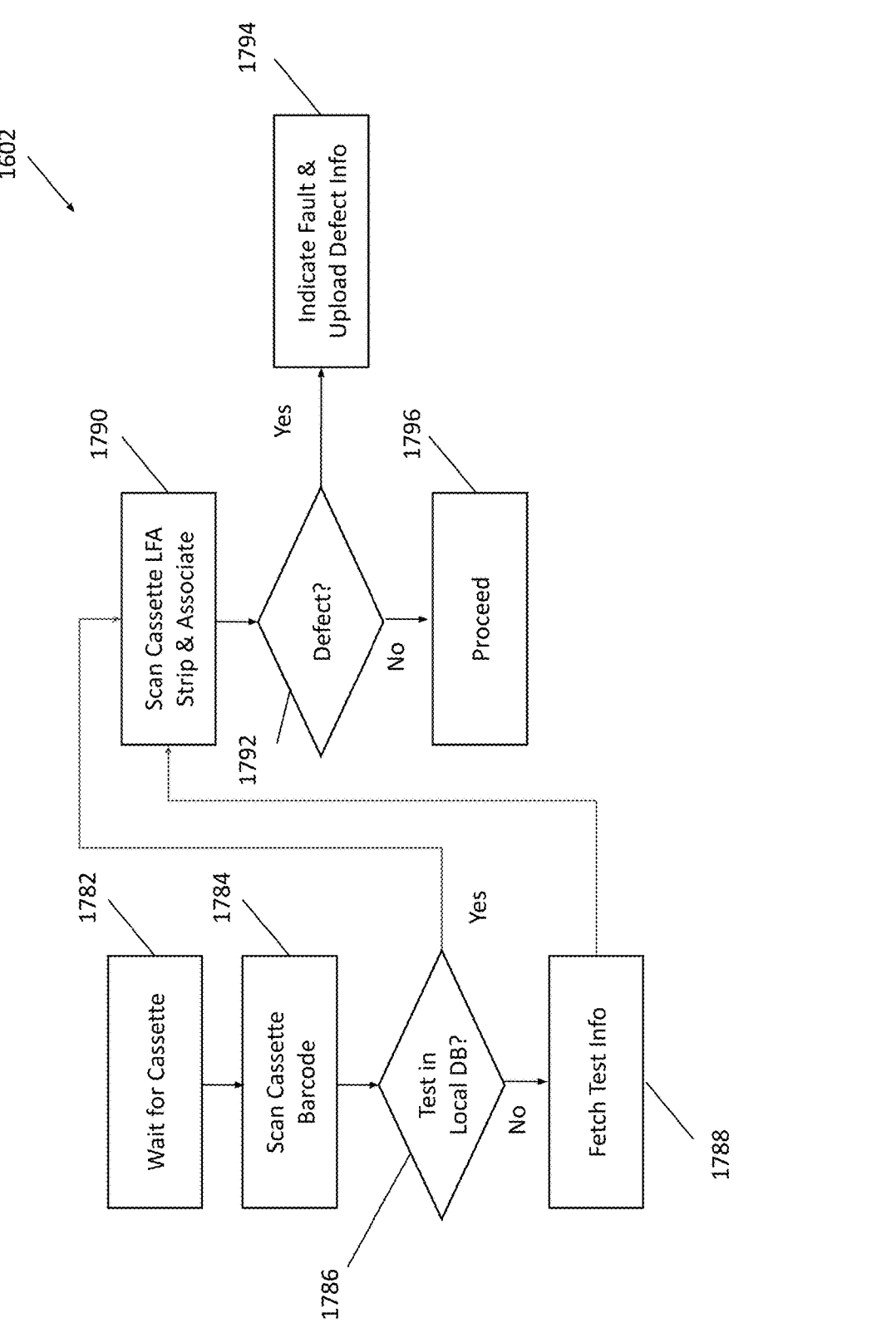
FIG. 17 depicts a flowchart of a method for performing an initial scan where an inserted cassette, clear assay or card is scanned for quality defects and association with a patient.

FIG. 17 depicts a flowchart of a method 1602 for performing an initial scan where an inserted cassette, clear assay or card is scanned for quality defects and association with a patient. The method waits for the detection of a clear assay, cassette, or card (block 1782). The method uses a camera to detect visual features, such a visual feature may be the shape of the inserted cassette, text on the cassette, presence or absence of one or more barcodes, data matrices or QR codes, or one or more colors present on the cassette, for example. In an alternative embodiment, the method may use a mechanical switch to detect the presence of a clear assay, cassette, or card. If there is no clear assay, cassette, or card, the method waits in a loop that may be, for example, 1 second long, until the detection of the clear assay, cassette, or card.

The method scans a visual feature off of the clear assay, cassette, or card to identify a test that is being conducted based on a visual feature and optionally a patient (block 1784). Identification of a vendor and specific test is made based on the visual feature. Following identification of the vendor and specific test, the test configuration profile is determined.

A check is made to determine if the test configuration profile is present in a local database (block 1786). Test configuration profiles are stored locally in, for example, an XML file. Each XML file may contain multiple test configuration profiles. If the test configuration profile is not present in the local database, a fetch is made to pull a configuration file from a central test database for storage in the local database (block 1488). Thus, new tests that are used in the field will cause the local database to update itself with information from the remote database.

The LFA strip is scanned (block 1790). To scan the LFA strip, the configuration file corresponding to the profile number provides brightness settings for LEDs that provide light at various wavelengths that will shine upon the LFA strip. The LEDs are turned on to that appropriate brightness level, and after a delay to permit the LEDs to arrive at the proper brightness and a camera to stabilize to take an image at that brightness level, images are taken by the camera. The number of images taken is indicated by the configuration file associated with the configuration profile. The areas of the LFA strip indicated by the profile to contain control and test lines are analyzed for color and intensity and results are averaged between several images taken to determine numerical values to be presented as results of the LFA strip scan. At this point, the method will read a patient's identification card that is inserted or scanned by the testing device 100 and locally store patient information that is then associated with the unique cassette identifier.

A machine learning engine, described in a following paragraph, that is pushed from the central test database analyzes the one or more images of the LFA strip and carrier in order to look for quality defects in the LFA strip and the cassette containing the LFA strip, such as: discoloration of the LFA strip; misalignment of the LFA strip within the cassette; breaks in the LFA strip; dust; debris on the LFA strip; plastic defects; and, defects in the visual feature (block 1792). If a defect is found that could affect the quality of the test result from reading the LFA strip, an error is generated and the one or more images of the LFA strip and carrier are stored, along with environmental information, such as temperature and humidity, a time stamp, and the specific nature of the quality defect.

The error triggers an alarm to an operator of equipment implementing this method, with the alarm identifying that there is an error with the LFA strip and carrier by setting an LFA read bad flag (block 1794). Furthermore, the information gathered based on the visual feature scanned earlier in the method, the images of the LFA strip and carrier, environmental information, time stamp, and specific nature of the quality defect are uploaded to the central test database. At the central test database the information received may be stored by the test kit vendor and may be supplied to the test kit vendor in order to provide quality control feedback. If no defects are found, information gathered is uploaded to the central test database (block 1796).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN)

or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method comprising:
    storing in a memory a local testing database having a test configuration profile, with the test configuration profile having an equivalence curve that associates an intensity value with a standardized test result, wherein the equivalence curve associates a plurality of intensity values with a plurality of equivalent cycle time ("eCt") values;
    receiving a lateral flow assay ("LFA") strip of a user to obtain a result value for the user from the LFA strip;
    reading the lateral flow assay ("LFA") strip using an LFA reader coupled to a processor to obtain an LFA strip image, the reading performed during a testing process to determine the result value for the user from the LFA strip;
    transmitting the LFA strip image to the processor;
    determining the result value for the LFA strip image by the processor, during the testing process, based on an intensity value of a portion of the LFA strip image using the equivalence curve in the memory, wherein using the equivalence curve comprises matching the intensity value of the portion of the LFA strip image with one of the plurality of intensity values of the equivalence curve to convert the matched intensity value to an eCt result value associated with the matched one of the plurality of intensity values.

2. The method of claim 1 further comprising:
    communicating with a central patient database using a communications interface;
    reading a patient identifier using an identity collection accessory;
    associating the result value with the patient identifier; and
    uploading the result value to the central patient database.

3. The method of claim 1, wherein the standardized test result is a value that corresponds to a cycle time of a polymerase chain reaction (PCR) testing.

4. The method of claim 1 wherein the reading is performed by an LFA strip reader comprises a plurality of LED lights activated based on the test configuration profile and a camera for reading the LFA strip and generating the LFA strip image.

5. The method of claim 4, wherein the plurality of LED lights includes visible and ultraviolet light.

6. The method of claim 1 further comprising: sterilizing at least a portion of an area within a carrier that receives the LFA strip using a light emitting device.

7. The method of claim 1, further comprising:
    building the equivalence curve for the LFA strip, the building comprising:
        receiving, by the processor, test information for the LFA strip, receiving, by the processor, the LFA strip image;
        receiving, by the processor, a known concentration of a viral load placed onto the LFA strip;

associating, by the processor, an intensity of a portion of the LFA strip image with the known concentration of the viral load placed onto the LFA strip and a standardized value;
repeating, by the processor, one or more previous steps until the equivalence curve is created.

8. The method of claim 1 wherein the LFA strip image comprises a plurality of columns, and the intensity value is determined by calculating a maximum median value of an intensity of pixels for each column of the plurality of columns.

9. A method, comprising:
receiving a lateral flow assay ("LFA") strip of a user to obtain a result value for the user from the LFA strip;
reading the lateral flow assay ("LFA") strip, using an imaging device, to generate an LFA strip image including a test line comprising a plurality of columns, the reading performed during a testing process to determine the result value for the user from the LFA strip;
determining, using a processor, during the testing process, a standardized test result based on an intensity value of a portion of the LFA strip image using an equivalence curve stored in a memory, wherein the equivalence curve associates a plurality of intensity values with a plurality of equivalent cycle time ("eCt") values, wherein using the equivalence curve comprises matching the intensity value of the portion of the LFA strip image with one of the plurality of intensity values of the equivalence curve to convert the matched intensity value to an eCt result value associated with the matched one of the plurality of intensity values; and
providing, using the processor, the standardized test result.

10. The method of claim 9, wherein the intensity value is determined, using the processor, by calculating a maximum median value of an intensity of pixels for each column of the plurality of columns.

11. The method of claim 10, wherein reading the LFA strip further comprises generating a plurality of LFA strip images.

12. The method of claim 11, wherein determining, using the processor, the standardized test result based on the intensity value further comprises determining a median value of the maximum median value of each of the plurality of LFA strip images.

13. The method of claim 9, further comprising:
associating the standardized test result with a patient identifier; and
sending to a central patient database the standardized test result associated with the patient identifier.

14. The method of claim 9 wherein the standardized test result is a value that corresponds to a cycle time of a polymerase chain reaction (PCR) testing.

15. The method of claim 9 further comprising:
building the equivalence curve for the LFA strip, the building comprising:
receiving, by the processor, test information for the LFA strip, receiving, by the processor, the LFA strip image;
receiving, by the processor, a known concentration of a viral load placed onto the LFA strip;
associating, by the processor, an intensity of a portion of the LFA strip image with the known concentration of the viral load placed onto the LFA strip and a standardized value;
repeating, by the processor, one or more previous steps until the equivalence curve is created.

16. The method of claim 9, wherein the processor is in a testing device and the equivalence curve is used by the processor to convert intensity measurements of the test line to an equivalent, standardized result.

17. A method comprising:
building an equivalence curve for a lateral flow assay ("LFA") strip, comprising:
receiving, by a processor, test information for the LFA strip,
receiving, by the processor, an image of the LFA strip;
receiving, by the processor, a known concentration of a viral load placed onto the LFA strip;
associating, by the processor, an intensity of a portion of the image of the LFA strip with the known concentration of the viral load placed onto the LFA strip and a standardized value;
repeating one or more previous steps, by the processor, using varying concentrations of viral load, until the equivalence curve is created; and
storing the equivalence curve in a memory;
receiving a second lateral flow assay ("LFA") strip of a user to obtain a result value for the user from the LFA strip;
reading the second lateral flow assay ("LFA") strip, using an imaging device, to generate an LFA strip image including a test line;
determining, using the processor, a result for the LFA strip image based on an intensity value of a portion of the LFA strip image using the equivalence curve that associates an intensity value with a standardized test result to generate the result value for the user, wherein the equivalence curve that associates an intensity value with a standardized test result comprises an equivalence curve that associates a plurality of intensity values with a plurality of equivalent cycle time ("eCt values"), and wherein using the equivalence curve comprises matching the intensity value of the portion of the LFA strip image with one of the plurality of intensity values of the equivalence curve to generate an eCt value associated with the matched one of the plurality of intensity values.

18. The method of claim 17, wherein the standardized value corresponds to a cycle time equivalent of a polymerase chain reaction (PCR) testing.

19. The method of claim 17, wherein the equivalence curve is created through linear regression.

* * * * *